United States Patent [19]

Lunnen et al.

[11] Patent Number: 5,366,882
[45] Date of Patent: Nov. 22, 1994

[54] METHOD FOR PRODUCING THE BGLI RESTRICTION ENDONUCLEASE AND METHYLASE

[75] Inventors: Keith D. Lunnen, Newbury; Geoffrey G. Wilson, Boxford, both of Mass.

[73] Assignee: New England Biolabs, Beverly, Mass.

[21] Appl. No.: 169,950

[22] Filed: Dec. 17, 1993

[51] Int. Cl.$^5$ .................... C12N 9/22; C12N 15/53; C12N 15/70
[52] U.S. Cl. ......................... 435/199; 435/193; 435/252.33; 435/320.1; 536/23.2
[58] Field of Search ............... 435/199, 320.1, 193, 435/252.33; 536/23.2

[56] References Cited

FOREIGN PATENT DOCUMENTS 193413 9/1986 European Pat. Off. .

OTHER PUBLICATIONS

Kosykh, et al., *Mole Gen. Genet.*, 178:717–719 (1980).
Wilson, *Gene*, 74:281–289 (1988).
Mann, *Gene*, 3:97–112 (1978).
Slatko, *Gene*, 74:45–50 (1988).
Walder, *PNAS*, 78:1503–1507 (1981).
Walder, *J. Biol. Chem.*, 258:1235–1241 (1983).
Bougueleret, et al., *Nucl. Acids Res.*, 12:3659–3676 (1984).
Lunnen, et al., *Gene*, 74:25–32 (1988).
Gingeras and Brooks, *PNAS*, 80:402–406 (1983).
Van Cott, *Gene*, 74:55–59 (1988).
Theriault and Roy, *Gene*, 19:355–359 (1982).
Raleigh & Wilson, *PNAS*, 83:9070–9074 (1986).
Blumenthal, *J. Bacteriol.*, 164:501–509 (1985).
Duncan, *J. Bacteriol.*, 134:338–355 (1978).
Kiss, et al., *Nucl. Acids. Res.*, 13:6403–6421 (1985).
Y. H. Lee, et al., *J. Biol. Chem.*, 254:6838–6841 (1979).
Szomolanyi, et al., *Gene*, 10:219–225 (1980).
Janulaitis, et al., *Gene*, 20:197–204 (1982).
Kiss and Baldauf, *Gene*, 21:111–119 (1983).

*Primary Examiner*—Charles L. Patterson, Jr.
*Attorney, Agent, or Firm*—David G. Conlin; Gregory D. Williams; David S. Resnick

[57] ABSTRACT

In accordance with the present invention there is provided an isolated DNA coding for the Bg/I restriction endonuclease and modification methylase derived from *Bacillus globigii* RUB561 stain, as well as related methods for cloning said recombinant DNA. The present invention also relates to clones which express recombinant Bg/I restriction endonuclease and recombinant modification methylase produced from Bg/I recombinant DNA and to methods for producing said enzymes.

7 Claims, 7 Drawing Sheets

FIG. I

```
   1 GAATTCTTTAGCAATTCATACGCATCCTGGGGTGACCGTATGGTTCTTTTCTTGTAAAGTATGCTAGACTCTTTAACTAATTAACTGAACTGAA
 107 ACAATATTGACTCTTTTGCCGAGGTATTTCCATTAAAATTCACTCCTAATAGAAAAATTAAAAGAGGAAGTTCACACGTCTACTAACGTGTG
 202 AACTTCCTCTCTTTATATCCCACTGTTATATAATATATTTGTATTTTTGA

251 AGATACGGGATAATGTTATAGACTTAAAGAGAATTTCATTCTCTTCTAATAGCAACTCCAATTGTTCAGCCTTCTTTTTCATCAGTAACACTG
                                  *  L  S  N  E  N  E  E  L  L  L  E  L  Q  E  A  K  K  E  D  T  V  S

348 TGATTGGTTTCTTAATTTTAGAAGCTTCTTTATTCCTACTTATGTAGAAAGTCTCCACATTTTATTAGAAAAGTTGAATGTATTCGGTTCTTTT
      H  N  T  E  K  I  K  S  A  E  K  N  R  S  I  Y  F  T  E  V  N  K  N  S  L  Q  I  Y  K  P  E  K  E

445 CTATACCTATAAAATTCCTTGATTCACTTAAAGCAGCTACAGCAGTTCCGCTTCCCATGAACAATCTAATACCGTATCTCCTTTTGAGTT
      I  G  I  F  N  R  S  E  S  L  A  A  V  A  T  T  G  S  G  M  F  C  D  L  V  T  D  G  K  Q  T

506 AGAAGTTTATCAACCTTTGAGGTAGTAAAGAGGGAACTTAGCTCATGGTCGTCTTCCTCACAGACGGGATATACCATATTCCTCTACT
      L  K  I  L  R  Q  P  L  L  L  P  F  K  A  E  H  D  D  N  K  R  V  S  P  I  Y  W  I  G  R  S

601 AGCCCAACTTGCCCATTCTTCTTCGATAGCTTATTTCTATCAATAACAGTCTCCAGGTTCCAAAATATATAAATGCTCAAATTCTGAAA
      A  W  S  A  W  E  E  K  S  L  K  N  R  D  I  V  T  E  G  P  K  W  F  I  Y  L  H  E  F  E  S  V

696 CGGCTTTATAAGAATTAGAAACAGGGCCTGCTAAATTTGCCAAGCAGGGTCTTAGCCCATATATTTCCGCCTGAATATATTTACCCTTCA
      A  K  Y  S  N  S  H  W  Q  S  N  Q  W  A  P  D  K  A  W  I  R  R  D  Y  L  Y  L  G  A  E  E

791 GCAGCTTTTCTAAAACAGGCCCTGCTAAATTTCACCTTAGTTGCACATTGGTATATTTCCGCCTGAATATATTTACCCTTTAATCTCTCTCAATT
      A  A  K  E  L  V  P  G  A  L  K  V  K  T  Q  V  N  Y  K  G  G  R  I  N  N  G  K  L  R  R  E  I

887 GTTTGTTCACTGCAATTAAACTTCTTGCCAATTGGTATTTGTTAACTCAGGTTGTTAAAGCATTAGTATATCTTCTTGTTACACTGA
      T  Q  E  S  C  N  F  K  K  A  L  Q  Y  K  T  L  E  P  E  L  K  L  A  N  L  I  D  E  R  T  V  S  V

984 CTCTATGTTCTTCAGGTTAACTGCTTGGAACCTTGGGTCAGGAGAATGCTAATATATCATGATGTTAATTACTAAAAACCACCT
      R  H  K  K  L  N  V  A  Q  F  R  P  M  R  P  D  P  F  A  L  I  D  D  I  N  V  L  F  G  G

1079 GGCTTTAGAATGGGATAATGCAACGCTATGACTTTGTTAAAAGTGATGACCATTGCTCGTATGTTGACCTTCTCATATTTTACCTACATGA
      P  K  L  I  P  Y  H  L  A  I  V  K  T  L  S  S  W  Q  E  Y  T  Q  G  E  E  Y  K  K  G  V  H
```

FIG. 5-1

```
1175 TAAGGGGGAGACCATACACTTAATGCAATACTCTCTTCTTCAATGCATTTTAATAATTCTCTAGCATCTCCTCATGAAAGGAGTTCTTTAA
      Y   P   P   S   W   V   S   L   A   I   S   E   E   E   I   C   K   L   L   E   R   A   D   G   E   H   F   S   N   K   K   L
1270 GTAACTATGGTTATTCATACATTTCCTCCAAAATAAAAACTCTAAATATCATTATATCCTGAATACCATTCACTTAACACATTGTACCT
                                                              M   Y   N   L   H   R   E   E   K   K   I
      Y   S   H   N   N   M  (SEQ ID NO:2)
1365 TTATTTACATTTAGTAATAATCTTTGTTCTCAATGTGTATAAATTAGTATAAGAGGTGAAATGAGAATTACACAGAGAAAAAT
      F   M   S   Y   N   Q   N   K   Q   Y   L   E   D   N   P   E   I   Q   E   K   I   E   L   Y   G   L   L   N   E
1460 CTTCATGTCCTATAATCAAATAAGCAATACTTAGAGGACAACCCTGAGATTCAAGAAAAAATTGAGCTGTATGGCTTAAACTTATTAAATGAA
      V   I   S   D   N   E   E   E   I   R   A   D   Y   N   E   A   N   F   L   H   P   F   W   M   N   Y   P   P   L   D   R
1554 GTAATTAGTGATAACGAAGAAGAAATACGCGCTGACTATAACGAAGCTAACTTCTTACATCCATTTTGGATGAATTATCCACCGTTAGACCGAG
      G   K   M   P   K   G   D   Q   I   P   W   I   E   V   G   E   K   A   V   G   S   K   L   T   R   L   V   S   Q   R   E
1648 GAAAAATGCCCAAAGGTGACCAGATACCATGGATAGAAGTTGGGGAAAAAGCTGTTGGGTCTAAGCTAACAAGACTGGTTTCTCAAGAGAAG
      D   I   T   V   R   E   I   G   L   P   T   G   P   D   E   R   Y   L   L   T   S   P   T   I   Y   S   L   T   N   G   F   T
1741 ATATAACAGTTAGAGAGAATAGGTCTTCCTACAGGACCTGATGAAAGATACTTGTTAACTTCTCCTACTATTTATAGCCTTACAAATGGATTACT
      D   S   I   M   M   F   V   D   I   K   S   P   N   Q   V   S   G   N   G
1836 GATTCAATAATGATGTTTGTTGATATCAAGTCCCCTAACCAAGTTCAGGAAACGG
      D   W   A   Q   L   E   G   G   I   Q   N   N   Q   T   I   Q   G   P   R   S   S   Q   F   L   P   T   I   P   P
1931 TGATTGGGCACAGTTAGAAGGTGGTATCCAAAATAATCAGCAACAATCCAAGGACCTCGTTCCTCACAAATATTCTTCCTACTATACCACCG
      L   Y   I   L   S   D   G   T   I   A   P   P   V   H   L   F   I   K   P   I   Y   A   M   R   S   L   T   K   G   D   T   G
2025 TTATATATTCTAAGTGATGGTACACAATTGCTCCAGTTGTGCATCTTTATCAAGCCGATTTACGGCTCGTAACTAAGGGAGATACGGG
      Q   S   L   Y   K   L   K   L   A   S   V   P   N   G   L   F   G   N   P   G   Y   A   F   D   S   A   Y   K   F   L
2120 ACAATCTCTTTATAAATTAAATTAGCATCTGTTCCTAATGGTTTTGGGTTTTGTTTGCAACCCAGGTTACGCATTTGACAGTGCTTATAAATTTT
      F   R   P   G   K   D   D   R   T   K   S   L   L   Q   K   R   V   R   V   D   L   R   V   L   D   K   I   G   P   R   V
2216 ATTCAGACCAGGTAAGATGATAGGACTAAGAGTTCGGGTTGACTTAAGAGTACTGGATAAGATTGGACCTAGAGAGTT
      M   T   I   D   M   D   K   *  (SEQ ID NO:3)
2310 ATGACAATTGATATGGATAAGTAAAAATGTAACTACAGAGAGAAGCAGCCTTCTTTATAACGATTGGCTG
```

FIG.5-2

```
2378 CTTTATTTCATAAAAACCTCATTTACTTATGGTACGGTTCCCACGATTAATCCGAAAAGCCGATAAATCTGCTCAACTAGTATGAGTCGCATCAA
2493 CTGATGAGGAAACGTCATCTTCGAGAAGAACAGTTTATCATCCGCTCGCTTCATCACCGGTCACTCGAGTGATCCGAGTGATCCGCCGATGACGAA
2586 GGTGACTTTGCTTTTTCCATAAGTAGCCAGCTTATCTATTGTATCGGCTAG
```

FIG. 5-3

METHOD FOR PRODUCING THE BGLI RESTRICTION ENDONUCLEASE AND METHYLASE

BACKGROUND OF THE INVENTION

The present invention relates to DNA encoding the Bg/I restriction endonuclease and modification methylase, and use of this DNA in the production of these enzymes.

Restriction endonucleases are a class of enzymes that occur naturally in bacteria. When they are purified away from other contaminating bacterial components, restriction endonucleases can be used in the laboratory to break DNA molecules into precise fragments. This property enables DNA molecules to be uniquely identified and to be fractionated into their constituent genes. Restriction endonucleases have proved to be indispensable tools in modern genetic research. They are the biochemical 'scissors' by means of which genetic engineering and analysis is performed.

Restriction endonucleases act by recognizing and binding to particular sequences of nucleotides (the 'recognition sequence') along the DNA molecule. Once bound, they cleave the molecule within, or to one side of, the sequence. Different restriction endonucleases have affinity for different recognition sequences. Close to one hundred different restriction endonucleases have been identified among the many hundreds of bacterial species that have been examined to date.

Bacteria tend to possess at most only a small number restriction endonucleases per species. The endonucleases typically are named according to the bacteria from which they are derived. Thus, the species *Haemophilus aegyptius*, for example synthesizes 3 different restriction endonucleases, named HaeI, HaeII and HaeIII. Those enzymes recognize and cleave the sequences (AT)GGCC(AT) (SEQ ID NO:4), PuGCGCPy (SEQ ID NO:5) and GGCC (SEQ ID NO:6) respectively. *Escherichia coli* RY13, on the other hand, synthesizes only one enzyme, EcoRI, which recognizes the sequence GAATTC (SEQ ID NO:7).

While not wishing to be bound by theory, it is thought that in nature, restriction endonucleases play a protective role in the welfare of the bacterial cell. They enable bacteria to resist infection by foreign DNA molecules like viruses and plasmids that would otherwise destroy or parasitize them. They impart resistance by scanning the lengths of the infecting DNA molecule and cleaving them each time that the recognition sequence occurs. The breakup that takes place disables many of the infecting genes and renders the DNA susceptible to further degradation by non-specific endonucleases.

A second component of bacterial protective systems are the modification methylases. These enzymes are complementary to restriction endonucleases and they provide the means by which bacteria are able to protect their own DNA and distinguish it from foreign, infecting DNA. Modification methylases recognize and bind to the same nucleotide recognition sequence as the corresponding restriction endonuclease, but instead of breaking the DNA, they chemically modify one or other of the nucleotides within the sequence by the addition of a methyl group. Following methylation, the recognition sequence is no longer bound or cleaved by the restriction endonuclease. The DNA of a bacterial cell is always fully modified, by virtue of the activity of its modification methylase and it is therefore completely insensitive to the presence of the endogenous restriction endonuclease. It is only unmodified, and therefore identifiably foreign, DNA that is sensitive to restriction endonuclease recognition and attack.

With the advent of genetic engineering technology, it is now possible to clone genes and to produce the proteins and enzymes that they encode in greater quantities than are obtainable by conventional purification techniques. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted, majority, of clones are destroyed while the desirable, rare, clones survive.

Type II restriction-modification systems are being cloned with increasing frequency. The first cloned systems used bacteriophage infection as a means of identifying or selecting restriction endonuclease clones [EcoRII: Kosykh, et al., *Molec. Gen. Genet.*, 178:717-719 (1980); HhaII: Mann, et al., *Gene*, 3: 97-112 (1978); PstI: Walder, et al., *Proc. Nat. Acad. Sci.*, 78:1503-1507 (1981)]. Since the presence of restriction-modification systems in bacteria enable them to resist infection by bacteriophages, cells that carry cloned restriction-modification genes can, in principle, be selectively isolated as survivors from libraries that have been exposed to phage. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids [EcoRV: Bougueleret, et al., *Nucl. Acid. Res.*, 12:3659-3676 (1984); PaeR7: Gingeras and Brooks, *Proc. Natl. Acad. Sci. USA*, 80:402-406 (1983); Theriault and Roy, *Gene*, 19:355-359 (1982); PvuII: Blumenthal, et al., *J. Bacteriol.*, 164:501-509 (1985)].

A third approach, and one that is being used to clone a growing number of systems involves cloning by selection for an active methylase gene [See, e.g., EPO Publication No. 193,413, published Sep. 3, 1986 and BsuRI: Kiss, et al., *Nucl. Acid. Res.*, 13:6403-6421 (1985)]. Since restriction and modification genes are often closely linked, both genes can often be cloned simultaneously. This selection does not always yield a complete restriction system however, but instead yields only the methylase gene (BspRI: Szomolanyi, et al., *Gene*, 10:219-225 (1980); BcnI: Janulaitis, et al, *Gene*, 20:197-204 (1982); BsuRI: Kiss and Baldauf, *Gene*, 21:111-119 (1983); and MspI: Walder, et al., *J. Biol. Chem.*, 258:1235-1241 (1983). See also Wilson, *Gene*, 74:281-289 (1988); Slatko, et al., *Gene*, 74:45-50 (1988); Lunnen, et al., *Gene*, 74:25-32 (1988); VanCott, et al, *Gene*, 74:55-59, (1988)].

There are, a number of possible explanations for such failures, and a variety of potential obstacles which the genetic engineer faces even in the methylase selection approach. In some systems the cloning problem may lie in trying to introduce the endonuclease gene into a host not already protected by modification. If the methylase gene and endonuclease gene are introduced on a common DNA fragment, the methylase gene must modify or protect the host before the endonuclease gene cleaves the host's genome.

Another obstacle to cloning these systems in *E. coli* was discovered in the process of cloning diverse methylases. Many *E. coli* strains (including those normally used in cloning) have systems that resist the introduction of DNA containing cytosine methylation. [See, Raleigh and Wilson, *Proc. Natl. Acad. Sci., USA*, 83:9070-9074 (1986)]. Therefore, it is also necessary to carefully consider which *E. coli* strain(s) to use for cloning.

Because highly purified restriction endonucleases, and to a lesser extent, modification methylases, are useful tools for characterizing and rearranging DNA in the laboratory, there is a commercial incentive to obtain strains of bacteria through recombinant DNA techniques that synthesize these enzymes in abundance. Such strains would be useful because they would simplify the task of purification as well as providing the means for production in commercially useful amounts.

SUMMARY OF THE INVENTION

In accordance with the present invention there is provided an isolated DNA coding for the Bg/I restriction endonuclease and modification methylase derived from *Bacillus globigii* RUB561 stain, as well as related methods for cloning said recombinant DNA. The present invention also relates to clones which express recombinant Bg/I restriction endonuclease and recombinant modification methylase produced from Bg/I recombinant DNA and to methods for producing said enzymes.

Bg/I is an enzyme which recognizes the DNA sequence GCCNNNN'NGGC (SEQ ID NO:8) and cleaves between the N4 and N5 residue. See, C. H. Duncan, et al., *J. Bacteriol*, 134:338-344 (1978); Y. H. Lee, et al., *J. Biol. Chem.*, 254:6838-6841 (1979), the disclosure of which is hereby incorporated by reference herein. Bg/I restriction endonuclease produced in accordance with the present invention is substantially pure and free of the contaminants normally found in Bg/I preparations made by conventional techniques, such as that disclosed by Duncan, et al., supra.

In accordance with the present invention, the cloning of the Bg/I RM system was complicated by several factors. First, it was discovered that Bg/I RM genes cannot be transferred in one step to a naive *E. coli* host. Attempts at making and selecting libraries in the traditional manner proved fruitless as far as isolating an intact (bg/IR) endonuclease gene linked to an intact methylase gene (bg/IM) (see FIG. 1). Establishing the BgII endonuclease gene (bg/IR) in *E. coli* had to be done in a multi-step manner, with one of the key factors being pre-modification of *E. coli* DNA by the Bg/I methylase (see FIG. 1 and 4). By isolating DNA from the strain, *B. globigii* RUB562 ($R_I^-M_I^+$)($R_{II}^+M_{II}^+$), a mutated strain in which the BgII endonuclease gene (bg/IR) had been inactivated, the present inventors were able to construct libraries, select for Bg/I methylase (M.Bg/I) expression and isolate clones carrying the BgII methylase gene (bg/IM) on a recombinant plasmid at a much higher frequency than from DNA libraries from *B. globigii* RUB561 ($R_I^+M_I^+$)($R_{II}^-M_{II}^+$) containing an intact (bg/IR) endonuclease gene.

Since it was impossible to clone the active bg/IR from the variant library, numerous additional steps proved necessary. These steps included: the preparation of an extremely pure sample of Bg/I endonuclease (R.Bg/I) from *B. globigii* RUB561; sizing the endonuclease protein and sequencing its amino terminus; designing corresponding DNA oligonucleotide probes; and looking for the hybridization of the probes to the bg/IM recombinant plasmid from *B. globigii* RUB561 ($R_I^+M_I^+$)($R_{II}^-M_{II}^+$) and generating DNA sequence. The whole region containing bg/IR was mapped onto the bg/IM plasmid; and both bg/IM and bg/IR were sequenced.

However, of the independently isolated Bg/I methylase clones that were sequenced, all contained different point mutations in bg/IR creating frameshift mutations that resulted in pre-mature stop codons. Because the frameshifts were in different locations in each independent clone, the present inventors developed a strategy to regenerate an intact bg/IR from two different Bg/I methylase plasmids. By using restriction enzyme sites mapped within the bg/IR, the point mutation of one bg/IM plasmid was deleted and replaced with DNA containing the intact orf of bg/IR from the other bg/IM clone. To establish an overexpressor of R.Bg/I, it was then necessary to manipulate the bg/IM clone further by subcloning bg/IM onto a separate comparable plasmid and transforming *E. coli*, thus creating a M.Bg/I pre-modified *E. coli* host. This *E. coli* host cell, was transformed by the regenerated bg/IR plasmid ligation and colonies were screened for R.Bg/I activity.

BRIEF DESCRIPTION OF THE DRAWINGS

FIGS. 5-1, 5-2, and 5-3 represent the nucleotide sequence coding for the Bg/I R-M system. The deduced amino acid sequence for the Bg/I methylase is set forth as SEQ ID NO:2 and the deduced N-terminal amino acid sequence for the Bg/I endonuclease is set forth as SEQ ID NO:3.

DETAILED DESCRIPTION OF THE INVENTION

The present invention relates to isolated DNA coding for the Bg/I restriction endonuclease and modification methylase, as well to methods of producing the Bg/I restriction endonuclease. The Bg/I genes of the present invention are cloned partly by a method which takes advantage of the fact that certain clones which are selected on the basis of containing and expressing the Bg/I modification or methylase gene also contain the Bg/I restriction gene. The DNA of such clones are resistant to digestion, in vitro, by the Bg/I restriction endonuclease. This resistance to digestion affords a means for selectively isolating clones encoding the Bg/I methylase and restriction endonuclease.

However, the cloning and expression of the Bg/I RM genes from *Bacillus globigii* RUB561 in *E. coli* proved to be difficult. As will be discussed in more detail below, in order to successfully produce R.Bg/I from a clone further steps beyond methylase selection were required.

Figure 1:
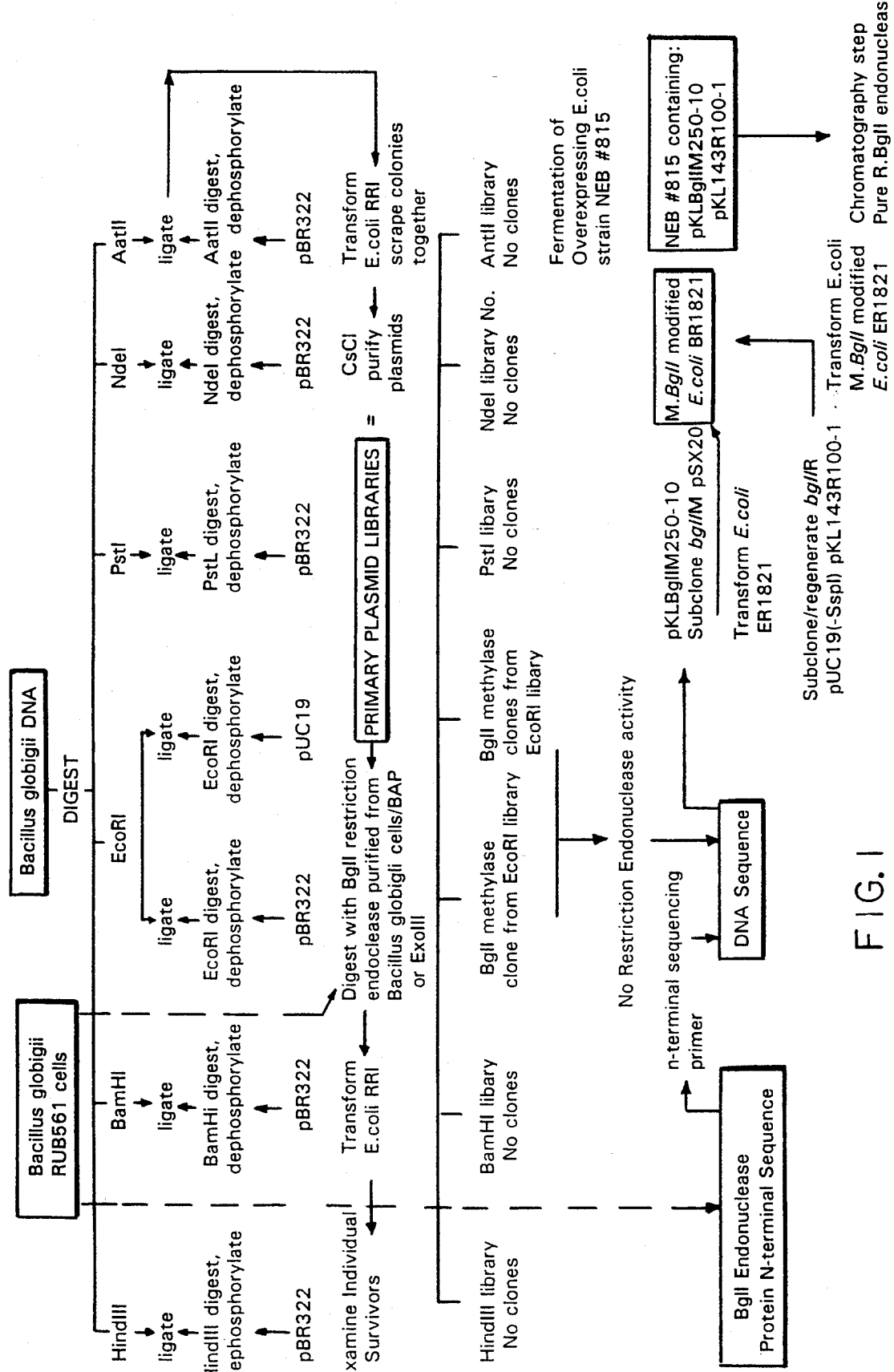
FIG. 1 illustrates the procedure for determining the preferred method for cloning the Bg/I methylase and identifying the Bg/I restriction endonuclease clones.
Figure 2:
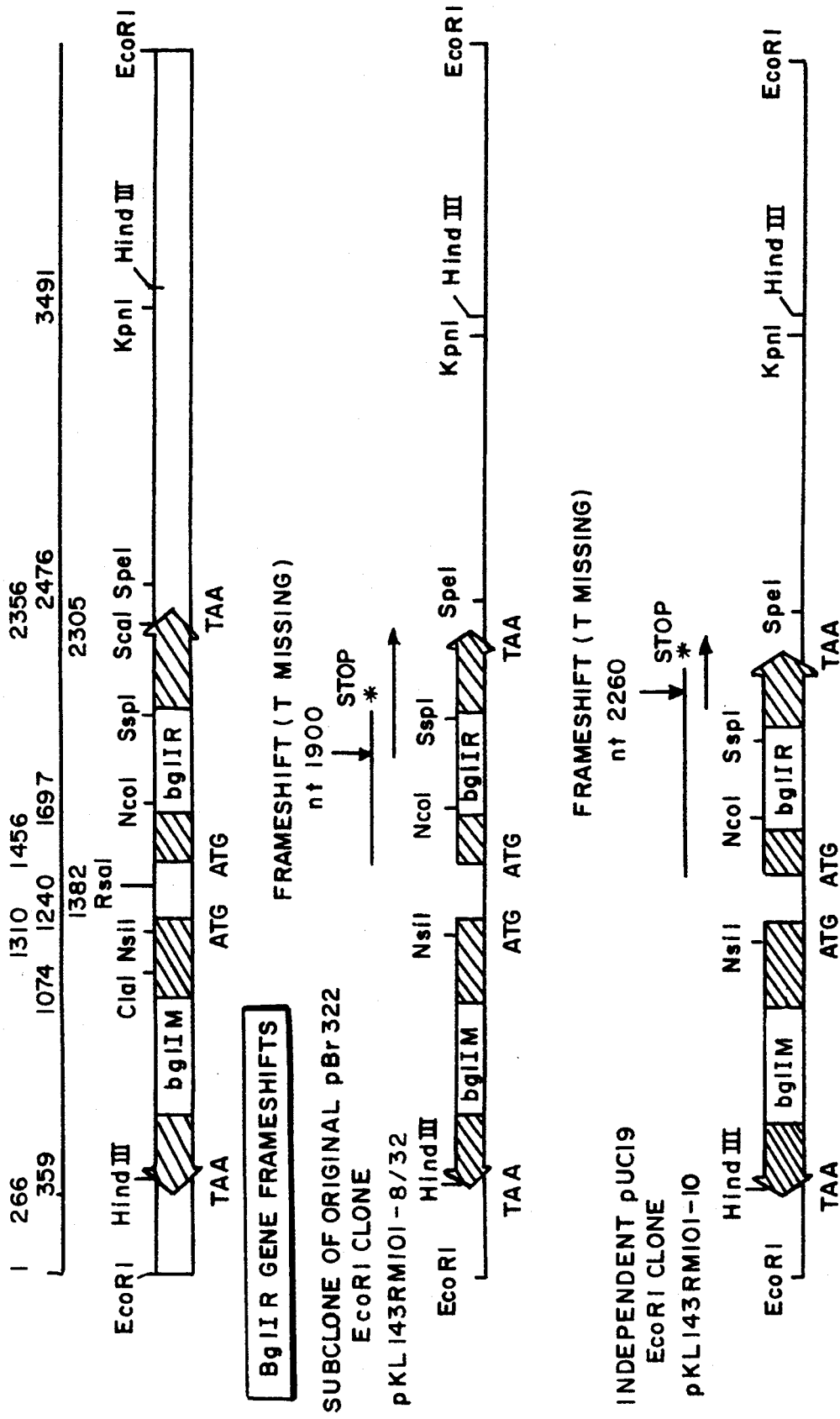
FIG. 2 is a restriction map of M.Bg/I clones and location of point mutations.
Figure 3:
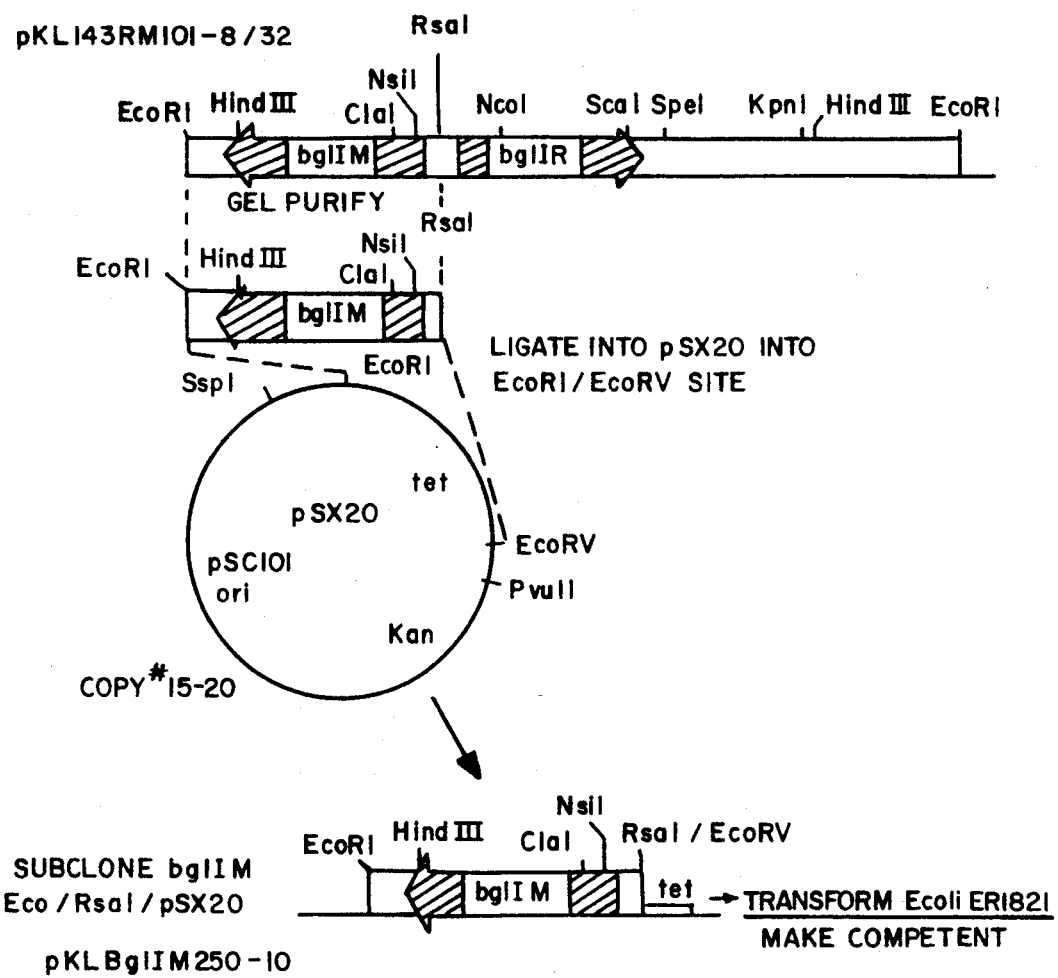
FIG. 3 illustrates the method for making M.Bg/I modified *E. coli* strain.
Figure 4:
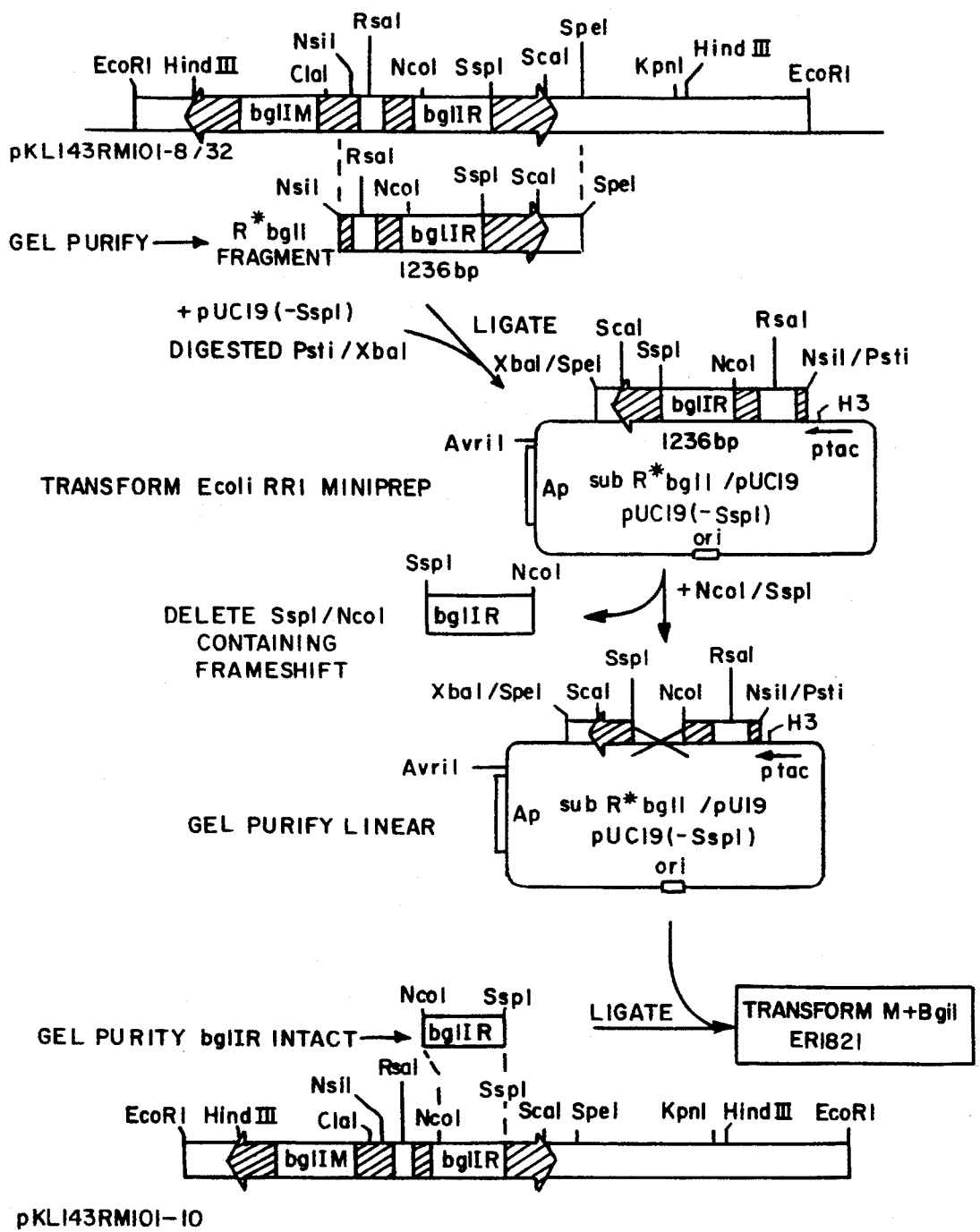
FIG. 4 illustrates the preferred method for cloning the BgII methylase and identifying the BgI I methylase and endonuclease clones.

The method described herein by which the Bg/I restriction gene and methylase gene are preferably cloned and expressed are illustrated in FIGS. 1, 3 and 4, and includes the following steps:

1. The DNA of *Bacillus globigii* RUB561 ($R_I^+M_I^+$)-($R_{II}^-M_{II}^+$) is purified. *Bacillus globigii* RUB561 has been described in a number of publications including; C. H. Duncan, et al., supra.
2. The DNA is digested partially with restriction endonucleases such as HindIII, EcoRI, BamHI, PstI, NdeI and AatII.
3. The digested DNAs from step 2 are ligated to a cloning vector, such as pBR322, pUC19, The resulting mixture is used to transform an appropriate host such as *E. coli* RR1 (ATCC No. 31343) cells. Note: Since EcoRI was the only digest to yield a bg/IM clone, the details for this work will be described. *Bacillus globigii* RUB562 ($R_I^-M_I^+$)($R_{II}^+M_{II}^+$) as described in; C. H. Duncan, et al., supra, was also used to clone bg/IM on pUC19. (See, Example 1).
4. The DNA/cell mixture is plated on antibiotic media selective for transformed cells, such as ampicillin. After incubation, the transformed cell colonies are collected together into a single culture, the primary cell library.
5. The recombinant plasmids are purified in toto from the primary cell library to make a primary plasmid library.
6. The plasmid library is then digested to completion in vitro with the Bg/I restriction endonuclease (New England Biolabs). Bg/I restriction endonuclease digestion causes the selective destruction of unmodified, non-methylase-containing, clones, resulting in an increase in the relative frequency of Bg/I methylase-carrying clones. Bacterial Alkaline Phosphatase or λ Exonuclease III can be used to enhance the destruction of non-methylated clones.
7. Identification of Bg/I methylase clones: The digested plasmid library DNA is transformed back into a convenient host such as *E. coli* strain RR1 (ATCC No. 31343), and transformed colonies are again obtained by plating on antibiotic plates. The colonies are picked and their DNA is analyzed for the presence of the Bg/I modification gene in the following manner: The plasmid DNA that they carry is purified and incubated in vitro with Bg/I restriction endonuclease to determine whether it is resistant to digestion by Bg/I. The total cellular DNA (chromosomal and plasmid) of the clone can also be purified and incubated with Bg/I restriction endonuclease. The DNA of clones that carry the Bg/I methylase gene should be fully modified, and both the plasmid DNA and the total DNA should be found to be substantially, or completely resistant to digestion.
8. Clones carrying the restriction endonuclease are usually identified by preparing crude extracts of those clones identified in step 7 as carrying the methylase gene, and assaying the extracts for restriction endonuclease activity. However, in all bg/IM clones isolated, no R.Bg/I activity was detected.
9. Locating the Bg/I endonuclease gene: R.Bg/I is extensively purified from *B. globigii* RUB561 cells to near-homogeneity. The purified protein migrates as a single band of approximately 32–36,000 Daltons on SDS polyacrylamide gels. It would therefore be encoded by a gene of approximately 900 bp.
The amino acid sequence of the N-terminal portion is determined. A degenerate oligonucleotide probe, specific for the 5' end of the endonuclease gene, is synthesized and labeled, e.g., radioactive, for use in hybridization experiments.
10. DNA sequence of the Bg/I RM system: Based on the N-terminal R.Bg/I protein sequence and Bacillus codon usage, a non-degenerate oligonucleotide probe is designed for about the first ten amino acids of R.Bg/I. DNA sequence is obtained from the bg/IM recombinant plasmid that verified the correct N-terminal protein sequence data. The bgl/R and bgl/M genes can be sequenced using various subclones. DNA sequence can be generated by priming and running using the dideoxy method using Klenow fragment of DNA polymerase I (New England Biolabs).
11. Preparation of a Bg/I methylase pre-modified *E. coli* strain: Using a clone, e.g., pUC19, containing the bg/IM gene fragment, an approximately 1382 bp EcoRI/RsaI fragment containing the bg/IM gene was cloned into the EcoRI/EcoRV site of pSX20, a derivative of pSC101 compatible with both pBR322 and pACYC-based plasmids. It has the pBR322 tetracycline resistance gene, pSC101 origin of replication, and a kanamycin resistance gene (FIG. 3). The bgl/M/pSX20 plasmid was isolated in *E. coli* RR1 and proven to be resistant to Bg/I endonuclease digestion. This recombinant methylase plasmid was then retransformed into an *E. coli* strain, e.g., ER1821 and made competent by standard methods.
12. Subcloning mutant bgl/R gene and deleting frameshift region: Using DNA sequence information, an approximately 1236 bp NsiI/SpeI fragment, containing the bgl/R gene from the 4.8 kb EcoRI fragment, was gel purified and subcloned into a pUC19 derivative lacking a SspI site at the PstI/XbaI sites in the polylinker region. (FIG. 4). The pUC19 derivative was made by inserting an 8 base AvrII linker (CCCTAGGG (SEQ ID NO:9)) into the SspI site of pUC19. In order to delete the bgl/R frameshift from this pUC19 derivative, the SspI site had to be missing. To delete the frameshift region, the NsiI/SpeI pUC19 recombinant plasmids were then digested with NcoI/SspI and then gel purified away from the smaller NcoI/SspI 325 bp fragment containing the frameshift.
13. Replacing mutant bg/IR with intact bg/IR: In parallel, another NcoI/SspI 325 bp fragment, lacking a bg/IR frameshift, and instead containing intact bg/IR orf was gel purified from an independent Bg/I methylase clone which was independently isolated from a pUC19 EcoRI library. The fact that this independent Bg/I methylase clone contained an intact bgl/R orf was shown as a result of DNA sequence data. The above gel purified DNA's were then mixed and ligated.
14. Overexpression of the bgl/R Gene: The DNA ligation in the previous section 13 was used to transform the M.Bg/I pre-modified *E. coli* ER1821 kanamycin resistant host as described in Section 11. The colonies containing the two plasmids for both bg/R and bg/IM were selected on ampicillin/kanamycin L-Broth plates at (100/50) μg/ml, respectively. Individual colonies were grown and the plasmid DNA's isolated were found to be resistant to Bg/I endonuclease digestion and also contained the 325 bp NcoI/SspI fragment containing an intact bg/IR orf. Endonuclease assays of crude extracts of these clones revealed a very high level of R.Bg/I greater than $10^6$ units/μg. The overproducing R.Bg/I *E. coli* strain was designated as NEB #815 and was deposited with the American Type Culture Collection on Dec. 8, 1993 and received ATCC Accession No. 69510.

15. Purification: The crude cell extract containing the Bg/I restriction endonuclease activity is purified by standard protein purification techniques such as affinity-chromatography, or ion-exchange chromatography.

Although the above-outlined steps represent the preferred mode for practicing the present invention, it will be apparent to those skilled in the art that the above described approach can vary in accordance with techniques known in the art.

The following examples are given to illustrate embodiments of the present invention as it is presently preferred to be practiced. It will be understood that the examples are illustrative, and that the invention is not to be considered as restricted thereto except as indicated in the appended claims.

EXAMPLE I

CLONING OF BgII RESTRICTION ENDONUCLEASE GENE

1. DNA Purification: To prepare the DNA of *Bacillus globigii* RUB561 ($R_I^+M_I^+$)($R_{II}^+M_{II}^+$), 5 g of frozen cells were thawed 1 hour on ice in 20 ml of 25% sucrose, 50 mM Tris, pH 8.0, 10 ml of 0.25M EDTA, pH 8 was added plus 6 ml 10 mg/ml lysozyme in 0.25M Tris, pH 8.0. The suspension was incubated on ice for 2 hours. To achieve cell lysis, 24 ml of lysis mix (1% Triton X-100, 50 mM Tris, 62 mM EDTA pH 5.0) and 5 ml 10% SDS was added. The sample was extracted with 70 ml of phenol, (previously equilibrated with 0.5M Tris pH 8.0), and then with 60 ml of chloroform. The emulsion was centrifuged at 10k rpm for 30 minutes. The viscous upper layer was withdrawn and dialyzed for 24 hours against 10 mM Tris, 1 mM EDTA, pH 8.0 (four buffer changes, 4 liters each). The dialyzed solution was then digested with RNase at a final concentration of 100 μ/ml for 1 hour at 37° C. The DNA was then harvested by adding NaCl to a final concentration of 0.4M, overlaying with 0.55 volumes of isopropyl alcohol, and spooling DNA onto a glass rod by mixing the phases together. The DNA was resuspended in 10 mM Tris, 1 mM EDTA, pH 8.0 to a final concentration of approximately 1,500 μg/ml stored at 4° C.

NOTE FOR STEPS 2–10

The details for constructing the EcoRI library using pBR322 will be the only library described. An EcoRI library using pUC19 also produced a methylase clone, however, details of this pUC19 clone will be described later since methylase selection and isolation of this clone was done in a similar fashion. The pBR322 and the pUC19 libraries were the only libraries that produced a restriction endonuclease and modification-methylase clone used to produce the Bg/I restriction endonuclease. As mentioned in the description herein, the bgl/R gene contained in both clones did not express the Bg/I endonuclease due to independent frameshift mutations in bg/IR. Other libraries made and selected in a similar fashion, did not produce Bg/I R-M clones. (See FIG. 1).

2. Partial and complete digestion: The purified DNA was cleaved with EcoRI to achieve partial and complete digestion as follows: 0.9 ml of DNA at 100 μg/ml in 10 mM Tris pH 7.5, 10 mM MgCl$_2$, 100 mM NaCl, 10 mM mercaptoethanol buffer was divided into one 200 μl aliquot and seven, 100 ul aliquots. To the 200 μl tube was added 80 units of EcoRI to achieve 4.0 units of enzyme per μg of DNA. 100 μl was withdrawn from the first tube and transferred to the second tube to achieve 2.0 EcoRI units/μg, and so on, each succeeding tube receiving half of the previous amount of EcoRI. The tubes were incubated at 37° C. for one hour, then heat-treated at 72° C. for 15 minutes and 15 μl from each was analyzed by agarose gel electrophoresis. Tubes exhibiting complete digestion were chosen as the source of complete digest fragments. (These were the 4.0 u/μg, 2.0 u/μg and 1.0 u/μg and 0.5 u/μg tubes) and tubes exhibiting partial digestion were chosen as the source for partial digest fragments for cloning. (These were the 0.2, 0.1, 0.05 and 0.02 tubes.) The solutions were mixed together and used as described below.

3. Ligation: The fragmented DNA was ligated to pBR322 as follows: 6.0 μg of EcoRI partially or completely digested *B. globigii* RUB561 DNA (60 μl) was mixed with 3.0 μg of EcoRI-cleaved and dephosphorylated pBR322 (30 μl). 20 μl of 10× ligation mix (500 mM Tris, pH 7.5, 100 mM MgCl$_2$, 100 mM DTT, 5 mM ATP) was added, plus 90 μl of sterile distilled water to bring the final volume to 200 μl. 7.5 μl of T4 DNA ligase was added and the mixture was incubated at 17° C. for 4 hours then sterilized by the addition of 10 ul of chloroform. Approximately 125 μl of the ligated DNA was used to transform *E. coli* strain RR1 as follows: The DNA was mixed with 1.0 ml of SSC/CaCl$_2$ (50 mM NaCl, 5 mM Na$_3$ Citrate, 67 mM CaCl$_2$) on ice and 2.0 ml of ice-cold competent *E. coli* RR1 (hsd R−M−, ATCC No. 31343) cells were added. After a 6-minute incubation at 42° C., followed by 5 minutes on ice, the cells were diluted by the addition of 9 ml of Luria-broth (L-broth) then incubated at 37° C. for 4 hours.

4. Primary Cell Library: The transformed cell culture was briefly centrifuged, the supernatant was discarded and the cells were resuspended in 1.0 ml of L-broth. 200 μl portions were plated onto Luria-agar (L-agar) plates containing 100 μg/ml ampicillin. After overnight incubation at 37° C., the plates were each flooded with 2.5 ml of 10 mM Tris, pH 7.5, 10 mM MgCl2 and the transformed colonies were scraped together and pooled to form the primary cell library.

5. Primary Plasmid Library: The primary plasmid library was prepared as follows: 2.5 ml of the primary cell library was inoculated into 500 ml of L-broth containing 100 μg/ml ampicillin. The culture was shaken overnight at 37° C. then centrifuged at 4000 rpm for 5 minutes. The supernatant was discarded and the cell pellet was resuspended in 10 ml of 25% sucrose, 50 mM Tris, pH 8.0, at room temperature. 5 ml of 0.25M EDTA, pH 8.0, was added, followed by 3 ml of 10 mg/ml lysozyme in 0.25M Tris, pH 8.0. The solution was left on ice for 1 hour, then 12 ml of lyric mix (1% Triton X-100, 50 mM Tris, pH 8.0, 67 mM EDTA) was forcefully pipetted in, and the cell suspension gently swirled to achieve lysis. After lysis, the mixture was transferred to a 50 ml plastic centrifuge tube and spun at 17000 rpm, 4° C. for 45 minutes. The supernatant was removed with a pipette. 20.0 gm of solid CsCl was weighed into a 50 ml plastic screw-cap tube and 22.0 gm of supernatant was pipetted into the tube and mixed. 1.0 ml of ethidium bromide solution (5 mg/ml ethidium bromide in 10 mM Tris, pH 8.0, 1 mM EDTA, 100 mM NaCl) was added to the mixture. The solution was transferred to two ⅜ in.×3 in. polyallomer centrifuge tubes and sealed. These tubes were then spun in a Beckman Ti70 rotor for 42 hours at 44000 rpm, 17° C. To collect the plasmids, the tops of the tubes were pierced with a scalpel and the lower of the two fluorescent DNA bands was collected by syringe under ultraviolet light. The lower band from both tubes was combined into a screw-top glass tube and the ethidium bromide was removed by extracting four times with an equal volume of water-saturated ice-cold N-Butanol.

The extracted solution was transferred to dialysis tubing and dialyzed for 24 hours against 4 changes of DNA buffer. The dialyzed DNA solution was then transferred to a pre-weighed 50 ml sterile centrifuge tube and its volume was measured. 5M NaCl was added to a final concentration of 0.4M, then 2 volumes of isopropanol were added and mixed. The solution was stored overnight at −20° C. to precipitate the DNA. After precipitation, the solution was spun at 15,000 rpm, 0° C. for 15 minutes and the supernatant discarded. The tube was left on the bench to air-dry for 15 minutes, then the DNA pellet was dissolved in 500 μl of DNA buffer and stored at −20° C. The DNA concentration of plasmids prepared in this way were found to be 100 to 200 μg/ml.

6. Digestion of Plasmid Pool: The primary plasmid pool was digested to destroy non-Bg/I methylase clones as follows: The plasmid DNA was diluted to 30 μg/ml in 10 mM Tris pH 7.5, 10 mM MgCl2, 10 mM mercaptoethanol, 100 mM NaCl in a volume of 900 μl and divided into one 300 μl aliquot and four, 150 μl aliquots. To the 300 μl tube was added 72 units of Bg/I to achieve 8.0 units of enzyme per μg of DNA. 150 μl was withdrawn from the first tube and transferred to the second tube to achieve 4.0 Bg/I units/μg, and so on, each succeeding tube receiving half of the previous amount of Bg/I. The tubes were incubated at 37° C. for 1 hour. The reactions were inactivated by heating to 72° C. for 10 minutes. 100 μl of each of the reaction mixtures was withdrawn. The DNA mixture was either treated with λ Exonuclease or Bacterial Alkaline Phosphatase. For λ Exonuclease the treatment is as follows: to each 100 μl tube 0.25 u/μg (0.5 μl at 1000 units/ml) of enzyme is added and the mixture is incubated at 37° C. for 30 minutes and 10 μl chloroform added. For BAP treatment, the DNA was precipitated by the addition of isopropanol. The precipitated DNA was collected by centrifugation and resuspended in 20 μl of DNA buffer (pH 9.0) to achieve approximately 150 μg DNA per ml. 0.4 units of bacterial alkaline phosphatase was added to each tube and each was incubated at 68° C. for two hours, under parafin oil. 80 μl of DNA buffer was added, mixed and removed. To this mixture 8 μl of chloroform was added and emulsified by vigorous mixing, and then separated by centrifugation.

7. Transformation: A 12.5 μl sample from each tube was used to transform *E. coli* RR1. The cell/DNA mixtures were plated onto L-agar plates containing 100 μg/ml ampicillin immediately after the heat step, without intermediate dilution and growth. After overnight incubation at 37° C., the plates were examined. Digestion of the plasmid library with Bg/I and λ exonuclease or bacterial alkaline phosphatase was found to have reduced the number of transformants by a factor of about $10^3$. Approximately 30 individual colonies were picked from the plates (8 units Bg/I/μg). Each colony was inoculated into 10 ml of L-broth containing ampicillin, to prepare a miniculture, and was also streaked onto L-agar plates containing ampicillin to prepare a master stock.

8. Analysis of surviving individuals: Approximately 30 of the surviving colonies from each library obtained from section 7 were grown up into 10 ml cultures (Section 7) and the plasmids that they carried were prepared by the following miniprep purification procedure, adapted from the method of Birnboin and Doly [*Nucleic Acids Res.* 7:1513 (1979)].

Miniprep Procedure: Each culture was centrifuged at 8000 rpm for 5 minutes; the supernatant was discarded and the cell pellet was resuspended in 1.0 ml of 25 mM Tris, 10 mM EDTA, 50 mM glucose, pH 8.0, containing 1 mg/ml lysozyme. After 10 minutes at room temperature, 2.0 ml of 0.2M NaOH, 1% SDS was added to each tube and the tubes were shaken to lyse the cells, then placed on ice. Once the solutions had cleared, 1.5 ml of 3M sodium acetate, pH 4.8, was added to each and shaken. The precipitates that formed were spun down at 15,000 rpm, 4° C. for 10 minutes. Each supernatant was poured into a centrifuge tube containing 3 ml of isopropanol and mixed. After 10 minutes at room temperature, the tubes were spun at 15,000 rpm for 10 minutes to pellet the precipitated nucleic acids. The supernatants were discarded and the pellets were air-dried at room temperature for 30 minutes. Once dry, the pellets were resuspended in 850 μl of 10 mM Tris, 1 mM EDTA, pH 8.0. 75 μl of 5M NaCl was added to each and the solutions were transferred to Eppendorf tubes containing 575 μl of isopropanol, and again precipitated for 10 minutes at room temperature. The tubes were then spun for 45 seconds in a microfuge, the supernatants were discarded and the pellets were air-dried. The pellets were then dissolved in 500 μl of 10 mM Tris, 1 mM EDTA, pH 8.0, containing 100 μg/ml RNase and incubated for 1 hour at 37° C. to digest the RNA. The DNA was precipitated once more by the addition of 50 μl of 5M NaCl followed by 350 μl of isopropanol. After 10 minutes at room temperature, the DNA was spun down by centrifugation for 45 seconds, the supernatants were discarded and the pellets were redissolved in a final solution of 150 μl of 10 mM Tris 1 mM EDTA, pH 8.0. The plasmid minipreps were subsequently analyzed by digestion with Bg/I.

Methylase Gene Clones: The majority of the plasmids that were analyzed were found to be sensitive to digestion by Bg/I endonuclease and to carry random fragments of B. globigii DNA. These plasmids were spurious survivors, of no further interest, and were discarded. 1 out of 28 plasmids from the pBR322 EcoRI library was found to be resistant to Bg/I and found to carry EcoRI fragments of approximately 4.8, 2.5, 1.0 Kb. This plasmid was subsequently shown to carry the Bg/I modification methylase gene but no restriction endonuclease gene activity was detected. 2 out of 26 plasmids from a pUC19EcoRI library were also found to be resistant to Bg/I digestion and also carried only the 4.8 kb EcoRI fragment. These plasmids carried the Bg/I modification methylase gene, but the Bg/I restriction endonuclease was not detected by assay of the crude extract. A restriction map of the 4.8 kb EcoRI fragment was made and the approximent location of the bg/IM gene was determined by subcloning, deletions, Southern blots and DNA sequencing. (See FIG. 3)

NOTE: Bg/I methylase selection of an EcoRI pUC19 library made from B. globigii strain RUB562 ($R_I^- M_I^+$)($R_{II}^+ M_{II}^+$), lacking an intact bg/IR gene yielded 26 methylase clones out of 28 that were resistant to Bg/I digestion and also carried the 4.8 kb EcoRI fragment. These results suggested that in order to establish a clone with an active bg/IR gene from B. globigii RUB561 ($R_I^+$-$M_I^+$)($R_{II}^+ M_{II}^+$) in E. coli, the E. coli host would need to be pre-modified against Bg/I endonuclease digestion before introducing an active bgl/R gene into the E. coli and/or bg/IR expression would need to be regulated. The latter turned out not to be the case. As would be predicted, the EcoRI clones from the RUB562 ($R_I^- M_I^+$)($R_{II}^+ M_{II}^+$) strain identified above as carrying the Bg/I modification methylase gene were also found not to carry detectable Bg/I restriction endonuclease activity.

9. Identifying the Restriction Gene: The location and orientation of the Bg/I endonuclease gene was determined using oligonucleotide primers derived from the amino-terminal sequence of the endonuclease protein. Bg/I endonuclease was purified to homogeneity from B. globigii RUB561 cells using standard protein purification techniques, The purified protein migrated as a single band of approximately 32,000–36,000 daltons on SDS-polyacrylamide gels. The gene encoding a protein of this size would about 900 bp. Protein sequence of the first 23 amino acid residues of the purified protein was determined by sequential degradation with Applied Biosystems 470A gas-phase sequenator, and was determined to be: Met Tyr Asn Leu His Arg Glu Lys Ile Trp Met Xaa Tyr Asn Xaa Asn Lys Gln Tyr Leu Xaa Asp Asn (SEQ ID NO:10). Based on protein sequence a 15mer degenerate oligonucleotide primer was made: 5'-GARAARATHTGGATG-3' (SEQ ID NO:11) and a 14mer probe: 5'-AAYAARCARTAYYT-3' (SEQ ID NO:12), where R=A or G, Y=C or T, H=A or C or T. Using Southern Blot hybridization analysis of pKL143RM101-8/32 plasmid and subclones, these degenerate probes localized the 5' end of the Bg/I endonuclease to the middle of the 4.8 kb EcoRI fragment.

Based on Bacillis codon usage another oligonucleotide primer was designed for sequencing that was non-degenerate: 5'-TGT ATAATTTACATAGAGAAAAAATTTGG-3' (SEQ ID NO:13).

The non-degenerate primer verified location of the Bg/I endonuclease and the predicted N-terminal protein sequence of the Bg/I endonuclease.

10. DNA sequencing the Bg/I R and M genes: The bgl/IR and bgl/IM genes were sequenced using various subclones of the 4.8 kb EcoRI fragment. The DNA sequence was generated by priming and running using the dideoxy method using Klenow fragment of DNA polymerase I (New England Biolabs). The DNA sequence coding for the Bg/I methylase and restriction endonuclease is set forth in the Sequence Listing as SEQ ID NO:1. The deduced amino acid sequence for the Bg/I methylase is set forth in FIG. 5 as SEQ ID NO:2. The deduced N-terminal amino acid sequence for the Bg/I endonuclease is set forth in FIG. 5 as SEQ ID NO:3. DNA sequencing revealed that bg/IM clones contained an inactive bg/IR gene due to point mutations causing a frameshift in each clone leading to a premature stop codon.

11. Preparation of Bg/1 methylase modified EcoliER1821: A pUC19 subclone, pKL143M 101-8/32, containing the 4.8 kb EcoRI fragment from the pBR322 Bg/I methylase clone, pKL143RM1-8, was digested with EcoRI/RsaI as follows: Approximately 10 ug of pKL143RM101-8/32 was diluted to approximately 100 μg/ml in 50 mM potassium acetate, 20 mM Tris acetate pH 7.9, 10 mM magnesium acetate, 1 mM dithiothreitol, acetylated BSA 100 μg/ml in a volume of 90 μl. 61 units of EcoRI and 35 units of RsaI was added to the mixture and incubated at 37° C. for 4 hours. 10 μl of the digestion mixture was analysed by gel electrophoresis to verify complete digestion.

Gel purification procedure: 20 μl of 4× loading dye was added to the digest and then all the volume was loaded on a 1% Agarose gel containing 0.01% SDS. The DNA was separated by gel electrophoresis, illuminated with long-wave UV and an approximately 1382 bp EcoRI/RsaI fragment was cut from the gel and minced using a clean razor blade. The mixture was forced through a 22 gauge syringe into 1 ml of 1×TE buffer (10 mM Tris pH 8.0, 1 mM EDTA), 0.01% SDS, and centifuged at 17,000 rpm for 45 minutes. The supernatent was precipitated with 0.1 ml 5M NaCl and 2.5 ml isopropanol at −20° C. overnight. The DNA was pelleted at 15,000 rpm for 15 minutes. The pellet was resuspended in 100 μl of 1×TE buffer, phenol/chloroform extracted, chloroform extracted two times and precipitated again with 10 μl 5M NaCl and 220 μl isopropanol at −20° C. overnight. The DNA was microfuged for 2 minutes, air dried, and resuspended in 50 μl of 1×TE buffer. 10 μl was analysed by gel electrophoresis and the gel pure 1382 bp EcoRI/RsaI fragment DNA concentration was determined to be approximately 30 μg/ml.

Ligation: The gel pure about 1382 bp EcoRI/RsaI fragment containing bg/IM was ligated to a pSX20 as follows: 0.5 μg of 1382 bp EcoRI/RsaI gel purified (30 μl) was mixed with 0.2 μg of EcoRI/EcoRV digested pSX20 (3 μl), 5 μl of 10× ligation buffer was added, plus 15 μl of sterile distilled water to bring the volume to 50 μl. 3.75 μl of T4 ligase was added and the mixture was incubated at 17° C. for overnight. 12.5 μl of ligated DNA was used to transform E. coli RR1 as follows: The DNA was mixed with 100 μl of SSC/CaCl₂ (50 mM NaCl, 5 mM Na₃Citrate, 67 mM CaCl₂) on ice and 200 μl of ice-cold competent E. coli RR1 cells were added. After a 3 minute incubation at 42° C., the cells were plated onto Luria-agar (L-agar) plates containing 50 μg/ml kanamycin. After overnight incubation at 37° C., individual colonies were struck onto L-agar plates containing kanamycin at 50 μg/ml and onto a separate L-agar plate containing tetracycline at 35 μg/ml and then the plates were incubated overnight at 37° C. Colonies containing inserts were selected for tetracycline sensitivity and kanamycin resistance. Plasmid DNA's from minipreps of 7 of the kanamycin resistant and tetracycline sensitive colonies were purified as described in section 8 and five of the seven were digested with Bg/I endonuclease. Three of these plasmids were found to be resistant to Bg/I endonuclease digestion and the others were not. The plasmids sensitive to BgII digestion did not contain the EcoRI/RsaI 1382 bp insert and presumably now contained an interrupted tetracycline gene. One of the 3 pSX20 EcoRI/RsaI bg/IM clones, pKLBgIIM250-10, was then retransformed into E. coli ER1821 and used to make competent M.Bg/I modified E. coli ER1821 using the standard CaCl₂ method.

12. Subcloning mutant bg/IR gene and deleting frameshift region: pKL143RM101-8/32, containing the 4.8 kb EcoRI fragment from the pBR322 Bg/I methylase clone, pKL143RM1-8, was again digested with NsiI/SpeI as follows: Approximately 10 μg of above plasmid was diluted to approximately 100 μg/ml in 50 mM Tris-HCl pH 7.7, 10 mM MgCl₂, 100 mM KCl in a volume of 90 μl. 35 units of NsiI and 10.5 units of SpeI was added to the mixture and incubated at 37° C. for overnight. The reaction was heated inactivated to 65° C. for 10 minutes. 10 μl of the digestion mixture was analysed by gel electrophoresis to verify complete digestion. The 1236 bp NsiI/SpeI fragment was gel purified using the procedure as described in Section 11.

Ligation: The gel pure 1236 bp NsiI/SpeI fragment containing bg/IR frameshift was ligated to a pUC19 derivative lacking an SspI site as follows: 0.5 μg of 1236 bp NsiI/SpeI gel purified (25 μl) was mixed with 0.2 μg of PstI/XbaI digested pUC19 (5 μl). 5 μl of 10× ligation buffer was added, plus 15 μl of sterile distilled water to bring the volume to 50 μl. 3.75 μl of T4 ligase was added and the mixture was incubated at 17° C. for overnight. 12.5 μl of ligated DNA was used to transform E. coli RR1 as follows: The DNA was mixed with 100 μl of SSC/CaCl₂ (50 mM NaCl, 5 mM Na₃Citrate, 67 mM CaCl₂) on ice and 200 μl of ice-cold competent E. coli RR1 cells were added. After a 3 minute incubation at 42° C., the cells were plated onto Luria-agar (L-agar) plates containing 100 μg/ml ampicillin. After overnight incubation at 37° C., 28 colonies were inoculated into 10 ml of L-Broth containing ampicillin, to prepare a miniculture, and each was also streaked onto L-agar plates containing ampicillin to prepare a master stock.

All 28 cultures were minipreped as described in Section 8. Fourteen plasmids were analysed by digestion with NcoI/SspI endonucleases to verify the presence of NsiI/SpeI insert since this NsiI/SpeI fragment could not be cut out directly due to being cloned into the PstI/XbaI sites. 14 out of the 14 minipreps analysed contained the mutant bg/IR NcoI/SspI fragment contained within the NsiI/SpeI fragment.

To delete the bg/IR frameshift, the remaining 3.6 kb NcoI/SspI fragment was gel purified away from the smaller 325 bp NcoI/SspI fragment. The 3.6 kb NcoI/SspI fragment contained the pUC19 derivative and the rest of the intact bg/IR.

13. Replacing mutant bg/IR with intact bg/IR: The DNA sequence of a another Bg/I methylase clone pKL143RM101-10, independently isolated from a pUC19 EcoRI library, revealed a different frameshift mutation in bg/IR located outside the NcoI/SspI sites near the 3' or carboxy end of bg/IR. Within the NcoI/SspI region of this particular clone, there was no mutation of bg/IR, so the NcoI/SspI 325 bp fragment was purified by digesting with NcoI/SspI as follows:

5 μg of pKL143RM101-10 plasmid DNA (70 μl) was mixed in 10 mM Tris pH 7.9, 10 mM MgCl₂, 1 mM dithiothreitol, 50 mM NaCl, BSA at 100 μg/ml, plus 10.1 μl of sterile distilled water to bring volume to 90 μl. 30 units of NcoI and 10 units of SspI was added and the mixture was incubated at 37° C. for 4 hr. The NcoI/SspI fragment containing intact bg/IR was electrophoresed and gel purified as previously described in Section 12.

Ligation: The gel pure NcoI/SspI plasmid/bg/IR fragment (lacking bg/IR frameshift mutation) isolated in Section 12 was ligated to the gel pure NcoI/SspI fragment from pKL143RM101-10 containing intact bg/IR orf as follows: 4 μl of NcoI/SspI plasmid/bg/IR fragment (0.2 μg) was mixed with 5 μl of 10× ligation buffer, 25 μl of NcoI/SspI fragment containing intact bg/IR orf (0.4 μg) and 16 μl of sterile distilled water to bring the volume to 50 μl. 3.75 μl of T4 ligase was added to the DNA mixture and incubated at 17° C. for overnight.

14. Overexpression of the Bg/I endonuclease: 12.5 μl of the ligated DNA mixture (Section 13) was used to transform E. coli ER1821 pre-modified with M.Bg/I (Section 11) as follows: The DNA was mixed with 100 μl of SSC/CaCl₂ (50 mM NaCl, 5 mM Na₃Citrate, 67 mM CaCl₂) on ice and 200 μl of ice-cold competent E. coli cells were added. After a 3 minute incubation at 42° C., the cells were plated onto Luria-agar (L-agar) plates containing 100 μg/ml ampicillin and 50 μg/ml kanamycin and then incubated overnight at 37° C. To identify the correct plasmid structure, 4 colonies were inoculated into 10 ml of L-broth containing 100 μg/ml of ampicillin and 50 μg/ml of kanamycin to prepare a miniculture, and each was streaked onto L-agar plates containing ampicillin and kanamycin to prepare a master stock. Plasmid DNA was isolated from each and digested with NcoI/SspI and Bg/I endonucleases. All 4 plasmid minipreps contained the 325 bp IVcol/SspI fragment as well as being fully resistant to Bg/I digestion. Crude extracts for 2 of the 4 colonies were analysed for expression of R.Bg/I endonuclease and shown to express bg/IR.

This was established by in vitro restriction endonuclease assays performed as follows:

Endonuclease Assays: To assay for endonuclease activity, two solutions were prepared: 10× restriction endonuclease buffer: 500 mM Tris, pH 7.5, 100 mM MgCl$_2$, 10 mM dithiothreitol, 1000 mM NaCl; and (ii) digestion reaction mix: 70 μl λ DNA (500 μg/ml), 7 μl 100× acetylated BSA, 70 μl 10× restriction endonuclease buffer, 553 μl distilled water to achieve 50 μg/ml DNA.

The cell extract was prepared as follows: A 100 ml culture of the clone to be tested was grown overnight in L-broth plus 100 μg/ml ampicillin and kanamycin 50 μg/ml at 37° C. and the cells were pelleted by centrifugation at 4,000 rpm for 5 minutes. The supernatant was discarded and the pellet was resuspended in 4 ml of sonication buffer (10 mM KPO$_4$ pH7.0, 10 mM BME, 0.1 mM EDTA, 100 mM NaCl). Once resuspended, 0.4 ml of sonication buffer containing 10 mg/ml lysozyme was added. The suspension was swirled and left on ice for 1 hour. A 1 ml sample was transferred to an Eppendorf tube and sonicated gently for three 30-second bursts to disrupt the cells. The tube was spun for 5 minutes in a microfuge and the supernatant was used as the cell extract. To assay the extract, the digestion reaction mix was dispensed into 5 tubes, 75 μl into the first tube and 50 μl into each of the remaining 4 tubes. 3.75 μl of the extract was added to the first tube and mixed. 25 μl was removed from the first tube and transferred to the second tube, mixed and so on. The first tube thus received 1 μl of extract per μg of DNA, the second tube 0.3 μl/μg, the third tube, 0.1 μl/μg and so on. The tubes, each now containing 50 μl, were incubated at 37° C. for one hour, then a 20 μl sample of each was analyzed by gel electrophoresis. The titre of the NEB #815 extract was found to be approximately 3×10$^6$ units of Bg/I restriction endonuclease per gram of wet cell paste. The R.Bg/I overexpressing E. coli strain, NEB #815, was deposited with the American Type Culture Collection on Dec. 8, 1993 and received ATCC Accession No. 69510.

The references cited throughout the specification are incorporated herein by reference.

This invention has been described in detail including the preferred embodiments thereof. However, it will be appreciated that those skilled in the art, upon consideration of this disclosure, may make modifications and improvements thereon without departing from the spirit and scope of the invention as set forth in the claims.

---

What is claimed is:

1. Isolated DNA coding for the Bg/I restriction endonuclease, wherein the isolated DNA is obtainable from ATCC Accession No. 69510.

2. A recombinant DNA vector comprising a vector into which a DNA segment coding for Bg/I endonuclease produced by *Bacillus globigii* has been inserted.

3. Isolated DNA coding from the Bg/I restriction endonuclease and methylase, wherein the isolated DNA is obtainable from ATCC Accession No. 69510.

4. A cloning vector which comprises a vector into which the isolated DNA of claim 1 has been inserted.

5. A cloning vector which comprises a vector into which the isolated DNA of claim 3 has been inserted.

6. A prokaryotic host cell transformed by the vector of claim 2, 4 or 5.

7. A method of producing Bg/I restriction endonuclease comprising culturing a prokaryotic host cell protected against Bg/I cleavage transformed with the vector of claim 2, 4 or 5 under conditions suitable for the expression of said endonuclease.

* * * * *

UNITED STATES PATENT AND TRADEMARK OFFICE
CERTIFICATE OF CORRECTION

PATENT NO. : 5,366,882
DATED : November 22, 1994
INVENTOR(S) : Lunnen, et. al.

It is certified that error appears in the above-identified patent and that said Letters Patent is hereby corrected as shown below:

Sheet 1 of 7, line 9 (Figure 1), replace "endoclease" with --endonuclease--.

Sheet 4 of 7, line 12 (Figure 4), replace "ptac" with --plac--.

Sheet 4 of 7, line 20 (Figure 4), replace "ptac" with --plac--.

Sheet 4 of 7, line 21 (Figure 4), replace "pU19" with --pUC19--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Cover page
Section [57], line 3, replace "Bg/I" with --*BgI*I--.

Cover page
Section [57], line 8, replace "Bg/I" with --*BgI*I--.

Cover page
Section [57], line 9, replace "Bg/I" with --*BgI*I--.

Column 1, line 8, replace "Bg/I" with --*BgI*I--.

Column 3, line 24, replace "Bg/I" with --*BgI*I--

Column 3, line 29, replace "Bg/I" with --*BgI*I--.

Column 3, line 30, replace "Bg/I" with --*BgI*I--.

Column 3, line 33, replace "Bg/I" with --*BgI*I--.

Column 3, line 39, replace "Bg/I" with --*BgI*I--.

Column 3, line 42, replace "Bg/I" with --*BgI*I--.

Column 3, line 45, replace "Bg/I" with --*BgI*I--.

Column 3, line 46, replace ""Bg/I" with --*BgI*I--.

Column 3, line 50, replace "(bg/IR)" with --(*bgI*IR)--.

Column 3, line 51, replace "(bg/IM)" with --(*bgI*IM)--

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 3, line 52, replace "(bg/IR)" with --(*bgl*IR)--.

Column 3, line 54, replace "Bg/I" with --*Bgl*I--.

Column 3, line 58, replace "(bg/IR)" with --(*bgl*IR)--.

Column 3, line 59, replace "Bg/I" with --*Bgl*I--.

Column 3, line 60, replace "(M.Bg/I)" with --(M.*Bgl*I)--.

Column 3, line 61, replace "(bg/IM)" with --(*bgl*IM)--.

Column 3, line 64, replace "(bg/IR)" with --(*bgl*IR)--.

Column 3, line 65, replace "bg/IR" with --*bgl*IR--.

Column 3, line 68, replace "Bg/I" with --*Bgl*I--.

Column 4, line 1, replace "(R.Bg/I)" with --(R.*Bgl*I)--.

Column 4, line 5, replace "bg/IM" with --*bgl*IM--.

Column 4, line 7, replace "bg/IR" with --*bgl*IR--.

Column 4, line 8, replace "bg/IM" with --*bgl*IM--.

Column 4, line 8, replace "bg/IM and bg/IR" with --*bgl*IM and *bgl*IR--.

Column 4, line 10, replace "Bg/I" with --*Bgl*I--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 4, line 12, replace "bg/IR" with --*bgl*IR--.

Column 4, line 16, replace "bg/IR" with --*bgl*IR--.

Column 4, line 16, replace "Bg/I" with --*Bgl*I--.

Column 4, line 18, replace "bg/IR" with --*bgl*IR--.

Column 4, line 19, replace "bg/IM" with --*bgl*IM--.

Column 4, line 20, replace "bg/IR" and "bg/IM" with --*bgl*IR-- and --*bgl*IM--.

Column 4, line 21, replace "R.Bg/I" with --R.*Bgl*I--.

Column 4, line 22, replace "bg/IM" with --*bgl*IM--.

Column 4, line 23, replace "bg/IM" with --*bgl*IM--.

Column 4, line 24, replace "M.Bg/I" with --M.*Bgl*I--.

Column 4, line 26, replace "bg/IR" with --*bgl*IR--.

Column 4, line 27, replace "R.Bg/I" with --R.*Bgl*I--.

Column 4, line 31, replace "Bg/I" with --*Bgl*I--.

Column 4, line 32, replace "Bg/I" with --*Bgl*I--.

Column 4, line 33, replace "M.Bg/I" with --M.*Bgl*I--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 4, line 35, replace "M.Bg/I" with --M.*Bg*lI--.

Column 4, line 38, replace "BgII" with --*Bg*lI--.

Column 4, line 41, replace "Bg/I" with --*Bg*lI--.

Column 4, line 42, replace "Bg/I" with --*Bg*lI--.

Column 4, line 44, replace "Bg/I" with --*Bg*lI--.

Column 4, line 50, replace "Bg/I" with --*Bg*lI--.

Column 4, line 51, replace "Bg/I" with --*Bg*lI--.

Column 4, line 52, replace "Bg/I" with --*Bg*lI--.

Column 4, line 56, replace "Bg/I" with --*Bg*lI--.

Column 4, line 57, replace "Bg/I" with --*Bg*lI--.

Column 4, line 58, replace "in vitro" and "Bg/I" with --*in vitro*-- and --*Bg*lI--.

Column 4, line 60, replace "Bg/I" with --*Bg*lI--.

Column 4, line 62, replace "Bg/I" with --*Bg*lI--.

Column 4, line 65, replace "R.Bg/I" with --R.*Bg*lI--.

Column 4, line 67, replace "Bg/I" with --*Bg*lI--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 5, line 6, replace "et al., supra" with --*et al., supra*--.

Column 5, lines 8 and 9, replace "HindIII, EcoRI, BamHI, PstI, NdeI and AatII" with --*Hind*III, *Eco*RI, *Bam*HI, *Pst*I, *Nde*I and *Aat*II--.

Column 5, line 14, replace "EcoRI" with --*Eco*RI--.

Column 5, line 15, replace "bg/IM" with --*bgl*IM--.

Column 5, line 17, replace "et al., supra" with --*et al., supra*--Column 5, line 18, replace "bg/IM" with --*bgl*IM--.

Column 5, line 18, replace, "bg/IM" with --*bgl*IM--.

Column 5, line 25, replace "in toto" with --*in toto*--.

Column 5, line 29, replace "in vitro" and "Bg/I" with --*in vitro*-- and --*Bgl*I--.

Column 5, line 30, replace "Bg/I" with --*Bgl*I--.

Column 5, line 34, replace "Bg/I" with --*Bgl*I--.

Column 5, line 37, replace "Bg/I" with --*Bgl*I--.

Column 5, line 43, replace "Bg/I" with --*Bgl*I--.

Column 5, line 45, replace "in vitro" and "Bg/I" with --*in vitro*-- and --*Bgl*I--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 5, line 47, replace "Bg/I" with --*Bgl*I--.

Column 5, line 49, replace "Bg/I" with --*Bgl*I--.

Column 5, line 51, replace "Bg/I" with --*Bgl*I--.

Column 5, line 60, replace "bg/IM" and "R.Bg/I" with --*bgl*IM-- and --R.*Bgl*I--.

Column 5, line 62, replace "Bg/I" and "R.Bg/I" with --*Bgl*I-- and --R.*Bgli*--.

Column 6, line 6, replace "Bg/I" with --*Bgl*I--.

Column 6, line 7, replace "R.Bg/I" with --R.*Bgl*I--.

Column 6, line 10, replace "R.Bg/I" with --R.*Bgl*I--.

Column 6, line 11, replace "bg/IM" with --*bgl*IM--.

Column 6, line 12, replace "bgl/R" with --*bgl*IR--.

Column 6, line 13, replace "bgl/M" with --*bgl*IM--.

Column 6, line 18, replace "Bg/I" with --*Bgl*I--.

Column 6, line 20, replace "bg/IM" with --*bgl*IM--.

Column 6, line 21, replace "EcoRI/RsaI" and "bg/IM" with --*Eco*RI/*Rsa*I-- and --*bgl*IM--.

Column 6, line 22, replace "EcoRI/EcoRV" with --*Eco*RI/*Eco*RV--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 6, line 27, replace "bgl/M" with --*bgl*IM--.

Column 6, line 29, replace "Bg/I" with --*BgI*--.

Column 6, line 33, replace "bgl/R" with --*bgl*IR--.

Column 6, line 35, replace "NsiI/SpeI" with --*NsiI/SpeI*--.

Column 6, line 36, replace "bgl/R" with --*bgl*IR--.

Column 6, line 37, replace "EcoRI" with --*Eco*RI--.

Column 6, line 38, replace "SspI" with --*SspI*--.

Column 6, line 39, replace "PstI/XbaI" with --*PstI/XbaI*--.

Column 6, line 42, replace "SspI" with --*SspI*--.

Column 6, line 43, replace "bgl/R" with --*bgl*IR--.

Column 6, line 44, replace "SspI" with --*SspI*--.

Column 6, line 45, replace "NsiI/SpeI" with --*NsiI/SpeI*--.

Column 6, line 46, replace "NcoI/SspI" with --*NcoI/SspI*--.

Column 6, line 47, replace "NcoI/SspI" with --*NcoI/SspI*--.

Column 6, line 49, replace "bg/IR with intact bg/IR" with --*bgl*IR with intact *bgl*IR--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 6, line 50, replace "NcoI/SspI" with --*Nco*I/*Ssp*I--.

Column 6, line 51, replace "bg/IR" with --*bgl*IR--.

Column 6, line 52, replace "bg/IR" with --*bgl*IR--.

Column 6, line 53, replace "Bg/I" with --*Bgl*I--.

Column 6, line 54, replace "EcoRI" with --*Eco*RI--.

Column 6, line 55, replace "Bg/I" with --*Bgl*I--.

Column 6, line 56, with --bgl/R" with --*bgl*IR--.

Column 6, line 59, replace "bgl/R" with --*bgl*IR--.

Column 6, line 61, replace "M.Bg/I" with --M.*Bgl*I--.

Column 6, line 64, replace "bg/R and bg/IM" with --*bgl*R and *bgl*IM--.

Column 6, line 68, replace "Bg/I" with --*Bgl*I--.

Column 7, line 1, replace "NcoI/SspI" with --*Nco*I/*Ssp*I--.

Column 7, line 2, replace "bg/IR" with --*bgl*IR--.

Column 7, line 4, replace "R.Bg/I" with --R.*Bgl*I--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 7, line 5, replace "R.Bg/I" with --R.*Bgl*I--.

Column 7, line 10, replace "Bg/I" with --*Bgl*I--.

Column 7, line 56, replace "EcoRI" with --*Eco*RI--.

Column 7, line 57, replace "EcoRI" with --*Eco*RI--.

Column 7, line 64, replace "Bg/I" with --*Bgl*I--.

Column 7, line 66, replace "bgl/R" with --*bgl*IR--.

Column 7, line 67, replace "Bg/I" with --*Bgl*I--.

Column 7, last line, replace "bg/IR" with --*bgl*IR--.

Column 8, line 1, replace "Bg/I" with --*Bgl*I--.

Column 8, line 4, replace "EcoRI" with --*Eco*RI--.

Column 8, line 10, replace "EcoRI" with --*Eco*RI--.

Column 8, line 13, replace "EcoRI" with --*Eco*RI--.

Column 8, line 14, replace "EcoRI" with --*Eco*RI--.

Column 8, line 27, replace "EcoRI" with --*Eco*RI--.

Column 8, line 29, replace "EcoRI" with --*Eco*RI--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 9, line 42, replace "Bg/I" with --*BgI*I--.

Column 9, line 48, replace "Bg/I" with --*BgI*I--.

Column 9, line 51, replace "Bg/I" with --*BgI*I--.

Column 9, line 52, replace "Bg/I" with --*BgI*I--.

Column 10, line 13, replace "Bg/I" with --*BgI*I--.

Column 10, line 17, replace "Bg/I" with --*BgI*I--.

Column 10, last line, replace "Bg/I" with --*BgI*I--.

Column 11, line 3, replace "Bg/I" with --*BgI*I--.

Column 11, line 7, replace "EcoRI" with --*Eco*RI--.

Column 11, line 8, replace "Bg/I" and "EcoRI" with --*BgI*I-- and --*Eco*RI--.

Column 11, line 10, replace "Bg/I" with --*BgI*I--.

Column 11, line 13, replace "EcoRI" with --*Eco*RI--.

Column 11, line 14, replace "Bg/I" with --*BgI*I--.

Column 11, line 15, replace "EcoRI" with --*Eco*RI--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 11, line 16, replace "Bg/I" and "Bg/I" with --*Bgl*I-- and --*Bgl*I--.

Column 11, line 19, replace "EcoRI" with --*Eco*RI--.

Column 11, line 20, replace "bg/IM" with --*bgl*IM--.

Column 11, line 23, replace "Bg/I" and "EcoRI" with --*Bgl*I-- and --*Eco*RI--.

Column 11, line 26, replace "bg/IR" with --*bgl*IR--.

Column 11, line 27, replace "Bg/I" with --*Bgl*I--.

Column 11, line 28, replace "EcoRI" with --*Eco*RI--.

Column 11, line 30, replace "bg/IR" with --*bgl*IR--.

Column 11, line 32, replace "Bg/I" with --*Bgl*I--.

Column 11, line 33, replace "bgl/R" with --*bgl*IR--.

Column 11, line 34, replace "bg/IR" with --*bgl*IR--.

Column 11, line 36, replace "EcoRI" with --*Eco*RI--.

Column 11, line 38, replace "Bg/I" with --*Bgl*I--.

Column 11, line 40, replace "Bg/I" with --*Bgl*I--.

Column 11, line 42, replace "Bg/I" with --*Bgl*I--.

Column 11, line 45, replace "Bg/I" with --*Bgl*I--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 11, line 67, replace "Bg/I" with --*BglI*--.

Column 11, last line, replace "EcoRI" with --*Eco*RI--.

Column 12, line 3, replace "5'-TGT     ATAATT-" with --5'-TGTATAATT--.

Column 12, line 7, replace "Bg/I" with --*BglI*--.

Column 12, line 8, replace "Bg/I" with --*BglI*--.

Column 12, line 9, replace "Bg/I" with --*BglI*--.

Column 12, line 10, replace "bgl/IR and bgl/IM" with --*bgl*IR and *bgl*IM--.

Column 12, line 11, replace "EcoRI" with --*Eco*RI--.

Column 12, line 15, replace "Bg/I" with --*BglI*--.

Column 12, line 18, replace "Bg/I" with --*BglI*--.

Column 12, line 21, replace "Bg/I" with --*BglI*--.

Column 12, line 22, replace "bg/IM" with --*bgl*IM--.

Column 12, line 23, replace "bg/IR" with --*bgl*IR--.

Column 12, line 26, replace "Bg/1" with --*BglI*--.

Column 12, line 28, replace "EcoRI" with --*Eco*RI--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 12, line 29, replace "Bg/I" with --*BgII*--.

Column 12, line 30, replace "EcoRI/RsaI" with --*Eco*RI/*Rsa*I--.

Column 12, line 36, replace "EcoRI" and "RsaI" with --*Eco*RI-- and --*Rsa*I--.

Column 12, line 45, replace "EcoRI/RsaI" with --*Eco*RI/*Rsa*I--.

Column 12, line 61, replace "EcoRI/RsaI" with --*Eco*RI/*Rsa*I--.

Column 12, line 64, replace "EcoRI/RsaI" with --*Eco*RI/*Rsa*I--.

Column 12, line 65, replace "bg/IM" with --*bgl*IM--.

Column 12, line 66, replace "EcoRI/RsaI" with --*Eco*RI/*Rsa*I--.

Column 12, lines 67-68, replace "EcoRI/EcoRV" with --*Eco*RI/*Eco*RV--.

Column 13, line 22, replace "Bg/I" with --*BgII*--.

Column 13, line 23, replace "Bg/I" with --*BgII*--.

Column 13, line 25, replace "BgII" with --*BgII*--.

Column 13, line 26, replace "EcoRI/RsaI" with --*Eco*RI/*Rsa*I--.

Column 13, line 28, replace "EcoRI/RsaI bg/IM" with --*Eco*RI/*Rsa*I *bgl*IM--.

Column 13, line 30, replace "M.Bg/I" with --M.*BgII*--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 13, line 33, replace "bg/IR" with --*bgl*IR--.

Column 13, line 36, replace "Bg/I" with --*Bgl*I--.

Column 13, line 37, replace "NsiI/SpeI" with --*Nsi*I/*Spe*I--.

Column 13, line 41, replace "NsiI" and "SpeI" with --*Nsi*I-- and --*Spe*I--.

Column 13, line 46, replace "NsiI/SpeI" with --*Nsi*I/*Spe*I--.

Column 13, line 49, replace "NsiI/SpeI" with --*Nsi*I/*Spe*I--.

Column 13, line 50, replace "bg/IR" with --*bgl*IR--.

Column 13, line 51, replace "SspI" with --*Ssp*I--.

Column 13, line 52, replace "NsiI/SpeI" with --*Nsi*I/*Spe*I--.

Column 13, line 53, replace "PstI/XbaI" with --*Pst*I/*Xba*I--.

Column 14, line 5, replace "NcoI/SspI" with --*Nco*I/*Ssp*I--.

Column 14, line 6, replace "NsiI/SpeI insert since this NsiI/SpeI" with --*Nsi*I/*Spe*I since insert this *Nsi*I/*Spe*I--.

Column 14, line 8, replace "PstI/XbaI" with --*Pst*I/*Xba*I--.

Column 14, line 9, replace "bg/IIR" with --*bgl*IIR--.

Column 14, line 10, replace "NcoI/SspI" with --*Nco*I/*Ssp*I--.

Column 14, lines 10 and 11, replace "NsiI/SpeI" with --*Nsi*I/*Spe*I--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 14, line 12, replace "bg/IR" with --*bgl*IR--.

Column 14, line 13, replace "NcoI/SspI" with --*NcoI/SspI*--.

Column 14, line 14, replace "NcoI/SspI" with --*NcoI/SspI*--.

Column 14, line 15, replace "NcoI/SspI" with --*NcoI/SspI*--.

Column 14, line 16, replace "bg/IR" with --*bgl*IR--.

Column 14, line 17, replace "bg/IR" with --*bgl*IR--.

Column 14, line 17, replace "bg/IR" with --*bgl*IR--.

Column 14, line 18, replace "Bg/I" with --*Bgl*I--.

Column 14, line 20, replace "EcoRI" with --*Eco*RI--.

Column 14, line 21, replace "bg/IR" with --*bgl*IR--.

Column 14, line 22, replace "NcoI/SspI" with --*NcoI/SspI*--.

Column 14, line 23, replace "bg/IR. Within the NcoI/SspI" with
            --*bgl*IR. Within the *NcoI/SspI*--.

Column 14, line 24, replace "bg/IR" with --*bgl*IR--.

Column 14, line 25, replace "NcoI/SspI" with --*NcoI/SspI*--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 14, line 26, replace "NcoI/SspI" with --*Nco*I/*Ssp*I--.

Column 14, line 31, replace "NcoI" and "SspI" with --*Nco*I-- and --*Ssp*I--.

Column 14, line 33, replace "NcoI/SspI" with --*Nco*I/*Ssp*I--.

Column 14, line 34, replace "bg/IR" with --*bgl*IR--.

Column 14, line 36, replace "NcoI/SspI plasmid/bg/IR" with
    --*Nco*I/*Ssp*I plasmid *bgl*IR--.

Column 14, line 37, replace "bg/IR" with --*bgl*IR--.

Column 14, line 39, replace "NcoI/SspI" with --*Nco*I/*Ssp*I--.

Column 14, line 40, replace "bg/IR" with --*bgl*IR--.

Column 14, line 41, replace "NcoI/SspI plasmid/bg/IR" with
    --*Nco*I/*Ssp*I plasmid *bgl*IR--.

Column 14, line 43, replace "NcoI/SspI" and "bg/IR" with --*Nco*I/*Ssp*I--
    and --*bgl*IR--.

Column 14, line 48, replace "Bg/I" with --*Bgl*I--.

Column 14, line 51, replace "M.Bg/I" with --M.*Bgl*I--.

Column 14, line 65, replace "NcoI/SspI and Bg/I" with --*Nco*I/*Ssp*I and
    *Bgl*I--.

Column 14, line 67, replace "IVcol/SspI" with --*Nco*I/*Ssp*I--.

UNITED STATES PATENT AND TRADEMARK OFFICE
CERTIFICATE OF CORRECTION

PATENT NO.: 5,366,882

DATED: November 22, 1994

INVENTOR(S): Lunnen, et al.

It is certified that errors appear in the above-identified patent and that said Letters Patent is hereby corrected as shown below:

Column 14, last line, replace "Bg/I" with --*Bgl*I--.

Column 15, line 2, replace "R.Bg/I" and "bg/IR" with --R.*Bgl*I-- and --*bgl*IR--.

Column 15, line 3, replace "in vitro" with --*in vitro*--.

Column 16, line 13, replace "Bg/I" with --*Bgl*I--.

Column 16, line 14, replace "R.Bg/I" with --R.*Bgl*I--.

Column 25, line 66, replace "Bg/I" with --*Bgl*I--.

Column 26, line 67, replace "Bg/I" with --*Bgl*I--.

Column 27, line 1, replace "Bg/I" with --*Bgl*I--.

Column 28, line 3, replace "Bg/I" with --*Bgl*I--.

UNITED STATES PATENT AND TRADEMARK OFFICE
CERTIFICATE OF CORRECTION

PATENT NO. : 5,366,882
DATED : November 22, 1994
INVENTOR(S) : Lunnen, et. al.

It is certified that error appears in the above-identified patent and that said Letters Patent is hereby corrected as shown below:

Column 28, line 5, replace "Bg/I" with --*Bg*II--.

Signed and Sealed this

Twelfth Day of January, 1999

Attest:

Attesting Officer    *Acting Commissioner of Patents and Trademarks*

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 3496 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:1:

```
GAATTCTTTT  AGCAATTCAT  ACGCATCCTG  GGGTGACCGT  ATGGTTCTTT  TCTTGTAAAG      60

TATGCTAGAC  TCTTTAACTA  ATTTAACTGA  ACTGAAACAA  TATTGACTCT  TTTTGCCGAG     120

GTATTTTCCA  TTAAAATTCA  CTCCTAATAG  AAAATTAAAA  AGAGGAAGTT  CACACGTCTA     180

CTTAACGTGT  GAACTTCCTC  TTTTATATCC  ACTGTTATAA  TATATATTTG  TATTTTTTGA     240

AGATACGGGA  TAATGTTATA  GACTTAAAGA  GAATTTTCAT  TCTCTTCTAA  TAGCAACTCC     300

AATTGTTCAG  CCTTCTTTTT  TTCATCAGTA  ACACTGTGAT  TGGTTTCTTT  AATTTTAGAA     360

GCTTCTTTAT  TCCTACTTAT  GTAGAAAGTC  TCCACATTTT  TATTAGAAAG  TTGAATGTAT     420

TTCGGTTCTT  TTTCTATACC  TATAAAATTC  CTTGATTCAC  TTAAAGCAGC  TACAGCAGTA     480

GTTCCGCTTC  CCATGAAACA  ATCTAATACC  GTATCTCCTT  TTTGAGTTAG  AAGTTTTATC     540

AACCTTTGAG  GTAGTAAAAG  AGGGAACTTA  GCCTCATGGT  CGTCGTTTTT  CCTCACAGAC     600

GGGATATACC  ATATTCCTCT  ACTAGCCCAA  CTTGCCCATT  CTTCTTTCGA  TAGCTTATTT     660

CTATCAATAA  CAGTCTCTCC  AGGTTTCCAA  AATATATATA  AATGCTCAAA  TTCTGAAACG     720

GCTTTATAAG  AATTAGAATG  CCATTGCGAA  TTTTGCCAAG  CAGGGTCTTT  AGCCCATATT     780

CTTCTATCAT  ATAAATACAA  GCCGGCTTCT  TCAGCAGCTT  TTTCTAAAAC  AGGGCCTGCT     840
```

```
AATTTCACCT TAGTTTGCAC ATTATATTTT CCGCCTCGAA TATTATTACC CTTTAATCTT    900
CTCTCAATTG TTTGTTCACT GCAATTAAAC TTCTTTGCCA ATTGGTATTT TGTTAACTCA    960
GGTTCCAATT TTAAAGCATT TAGTATATCT TCTCTTGTTA CACTGACTCT ATGTTTCTTC   1020
AGGTTAACTG CTTGGAACCT TGGCATCCTT GGGTCAGGGA ATGCTAATAT ATCATCGATG   1080
TTAATTACTA AAAACCACC TGGCTTTAGA ATGGGATAAT GCAACGCTAT GACTTTTGTT    1140
AAAAGTGATG ACCATTGCTC GTATGTTTGA CCTTCTTCAT ATTTTTACC TACATGATAA    1200
GGGGGAGACC ATACACTTAA TGCAATACTC TCTTCTTCAA TGCATTTTAA TAATTCTCTA   1260
GCATCTCCTT CATGAAAGGA GTTCTTCTTT AAGTAACTAT GGTTATTCAT ACATTTCCTC   1320
CAAAATAAAA ACTCTAAATA TCATTATATC AATTCCTCGA ATACCATTCA CTTAACACAT   1380
TGTACCTTTA TTTACATTTA GTAATTAATC TTTGTTTCTC AATGTGGTAT AAATTAGTAT   1440
AAGAGGTGAA ATGAGAATGT ATAATTTACA CAGAGAAAAA ATCTTCATGT CCTATAATCA   1500
AAATAAGCAA TACTTAGAGG ACAACCCTGA GATTCAAGAA AAAATTGAGC TGTATGGCTT   1560
AAACTTATTA AATGAAGTAA TTAGTGATAA CGAAGAAGAA ATACGCGCTG ACTATAACGA   1620
AGCTAACTTT CTACATCCAT TTTGGATGAA TTATCCACCG TTAGACCGAG GAAAAATGCC   1680
CAAAGGTGAC CAGATACCAT GGATAGAAGT TGGCGAAAAA GCTGTTGGGT CTAAGCTAAC   1740
AAGACTTGTT TCTCAAAGAG AAGATATAAC AGTTAGAGAG ATAGGTCTTC CTACAGGACC   1800
TGATGAAAGA TACTTGTTAA CTTCTCCTAC TATTTATAGC CTTACAAATG GATTACTGA    1860
TTCAATAATG ATGTTTGTTG ATATTAAATC AGTTGGCCCT AGAGACAGTG ATTACGATTT   1920
AGTATTGTCC CCTAACCAAG TTTCAGGAAA CGGTGATTGG GCACAGTTAG AAGGTGGTAT   1980
CCAAAATAAT CAGCAAACAA TCCAAGGACC TCGTTCCTCA CAAATATTTC TTCCTACTAT   2040
ACCACCGTTA TATATTCTAA GTGATGGTAC AATTGCTCCA GTTGTGCATC TTTTTATCAA   2100
GCCGATTTAC GCCATGCGCT CGCTAACTAA GGGAGATACG GGACAATCTC TTTATAAAAT   2160
TAAATTAGCA TCTGTTCCTA ATGGTTTGGG TTTGTTTTGC AACCCAGGTT ACGCATTTGA   2220
CAGTGCTTAT AAATTTTTAT TCAGACCAGG TAAAGATGAT AGGACTAAAT CACTTTTGCA   2280
AAAAAGGGTT CGGGTTGACT TAAGAGTACT GGATAAGATT GGACCTAGAG TTATGACAAT   2340
TGATATGGAT AAGTAAAATG TAACTACAGA GAAGCAGCCT TTCTTTATAA CGATTGGCTG   2400
CTTTATTTCA TAAAAACCTC ATTTACTTAT GGTACGGTTC CCACGATTAA TCCGAAAAGC   2460
CGATAAATCT GCTCAACTAG TATGAGTCGC ATCAACTGAT GAGGAAACGT CATCTTCGAG   2520
AACGAACAGT TTATCATCCG CTCGCTTCAT CACCGCGTCA CTCAATCCGA GTGATCCGCC   2580
GATGACGAAG GTGACTTTGC TTTTTCCATA AGTAGCCAGC TTATCTATTG TATCGGCTAG   2640
TTCTTCGGAT GTTTTCATTT TTCCTTCGAT GGCGAGGGCG ATGACGTGGG CGTCGGGGCT   2700
GATTTTGAT AGGATGCGGT CGCCTTCTTT GTCTTTATG ATTTTCATGT CCTGGTCGCT    2760
TAGATTTTCC GGCGCTTTTT CGTCCGGTAG TTCGATGATG TCGATTTTTG CGTAGGCCGA   2820
AAGTCGTTTT GTGTATTCTT CAATTCCTTG CTTGAGGTAT TTTTCTTTTA GTTTCCGAT    2880
TGTCACAATA TTGATATTCA CAGGTCATCC CCACCTTAGA AACAAGTTAT TCATATATGT   2940
TGTCCACATT TGTGGATATC TTTTCTGTAT TTTGTGTAAG ATCATTCGTT CCCCACTATA   3000
TATACTGCGG GCTCACTACA TAATTCACAG GCTGTGGATA AACTGTTAGT ATGTTCGATT   3060
TTTCTGATTT CGGGCGGGAG TTCGTGGTCG TCTATGTACA TATCCAGCAC GGTTCGATG    3120
TGTTCTTCAC AGGAATAATA AGCATTTTTC ATTTTTAGTC CTCCGATGTT TTCTTGCATT   3180
CTGCAAATGT TCTCTTCCCA ATATAACCTA TTTATTCACA TGTTAGTAGT GCTTCGGGCT   3240
GAGTTTTATC CACAATTCGA CAAGCGAAGC TGTTGATGAC TCTATTTCGT CCGTATGTTA   3300
```

-continued

```
GTTTTGATGT AACCGAAGTT TGGGGAGGTC TGCATTTGAA ACTCAGATGG GTGTGGCTTT      3360

TCGTGATCAT GTTGTTGCTT GCTGCGTGTC ACCCAGTCTT ATTGGGTGTT AGAGAAGGAT      3420

CGGATCGGTG AAGGCAGTTC CGAGCTAGAA TTATATGCAA ATTATCTTCA AACACATGAA      3480

AACGTAATAG GGTACC                                                     3496
```

( 2 ) INFORMATION FOR SEQ ID NO:2:

( i ) SEQUENCE CHARACTERISTICS:
        ( A ) LENGTH: 348 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:2:

```
Leu Ser Asn Glu Asn Glu Glu Leu Leu Leu Glu Leu Gln Glu Ala Lys
 1           5                  10                 15

Lys Lys Glu Asp Thr Val Ser His Asn Thr Glu Lys Ile Lys Ser Ala
             20                  25                 30

Glu Lys Asn Arg Ser Ile Tyr Phe Thr Glu Val Asn Lys Asn Ser Leu
         35                  40                 45

Gln Ile Tyr Lys Pro Glu Lys Glu Ile Gly Ile Phe Asn Arg Ser Glu
     50                  55                  60

Ser Leu Ala Ala Val Ala Thr Thr Gly Ser Gly Met Phe Cys Asp Leu
65                  70                  75                  80

Val Thr Asp Gly Lys Gln Thr Leu Leu Lys Ile Leu Arg Gln Pro Leu
                 85                  90                  95

Leu Leu Pro Phe Lys Ala Glu His Asp Asp Asn Lys Arg Val Ser Pro
            100                 105                 110

Ile Tyr Trp Ile Gly Arg Ser Ala Trp Ser Ala Trp Glu Glu Lys Ser
        115                 120                 125

Leu Lys Asn Arg Asp Ile Val Thr Glu Gly Pro Lys Trp Phe Ile Tyr
    130                 135                 140

Leu His Glu Phe Glu Ser Val Ala Lys Tyr Ser Asn Ser His Trp Gln
145                 150                 155                 160

Ser Asn Gln Trp Ala Pro Asp Lys Ala Trp Ile Arg Arg Asp Tyr Leu
                165                 170                 175

Tyr Leu Gly Ala Glu Glu Ala Ala Lys Glu Leu Val Pro Gly Ala Leu
            180                 185                 190

Lys Val Lys Thr Gln Val Asn Tyr Lys Gly Gly Arg Ile Asn Asn Gly
        195                 200                 205

Lys Leu Arg Arg Glu Ile Thr Gln Glu Ser Cys Asn Phe Lys Lys Ala
    210                 215                 220

Leu Gln Tyr Lys Thr Leu Glu Pro Glu Leu Lys Leu Ala Asn Leu Ile
225                 230                 235                 240

Asp Glu Arg Thr Val Ser Val Arg His Lys Lys Leu Asn Val Ala Gln
                245                 250                 255

Phe Arg Pro Met Arg Pro Asp Pro Phe Ala Leu Ile Asp Asp Ile Asn
            260                 265                 270

Ile Val Leu Phe Gly Gly Pro Lys Leu Ile Pro Tyr His Leu Ala Ile
        275                 280                 285

Val Lys Thr Leu Leu Ser Ser Trp Gln Glu Tyr Thr Gln Gly Glu Glu
    290                 295                 300

Tyr Lys Lys Gly Val His Thr Pro Pro Ser Trp Val Ser Leu Ala Ile
305                 310                 315                 320

Ser Glu Glu Glu Ile Cys Lys Leu Leu Glu Arg Ala Asp Gly Glu His
```

325                          330                          335
        Phe  Ser  Asn  Lys  Lys  Leu  Tyr  Ser  His  Asn  Asn  Met
                       340                     345

( 2 ) INFORMATION FOR SEQ ID NO:3:

( i ) SEQUENCE CHARACTERISTICS:
        ( A ) LENGTH: 299 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:3:

Met  Tyr  Asn  Leu  His  Arg  Glu  Lys  Ile  Phe  Met  Ser  Tyr  Asn  Gln  Asn
    1                   5                        10                       15

Lys  Gln  Tyr  Leu  Glu  Asp  Asn  Pro  Glu  Ile  Gln  Glu  Lys  Ile  Glu  Leu
                   20                        25                       30

Tyr  Gly  Leu  Asn  Leu  Leu  Asn  Glu  Val  Ile  Ser  Asp  Asn  Glu  Glu  Glu
                   35                   40                       45

Ile  Arg  Ala  Asp  Tyr  Asn  Glu  Ala  Asn  Phe  Leu  His  Pro  Phe  Trp  Met
         50                        55                       60

Asn  Tyr  Pro  Pro  Leu  Asp  Arg  Gly  Lys  Met  Pro  Lys  Gly  Asp  Gln  Ile
    65                        70                        75                            80

Pro  Trp  Ile  Glu  Val  Gly  Glu  Lys  Ala  Val  Gly  Ser  Lys  Leu  Thr  Arg
                        85                        90                       95

Leu  Val  Ser  Gln  Arg  Glu  Asp  Ile  Thr  Val  Arg  Glu  Ile  Gly  Leu  Pro
                        100                      105                      110

Thr  Gly  Pro  Asp  Glu  Arg  Tyr  Leu  Leu  Thr  Ser  Pro  Thr  Ile  Tyr  Ser
                   115                      120                      125

Leu  Thr  Asn  Gly  Phe  Thr  Asp  Ser  Ile  Met  Met  Phe  Val  Asp  Ile  Lys
              130                      135                      140

Ser  Val  Gly  Pro  Arg  Asp  Ser  Asp  Tyr  Asp  Leu  Val  Leu  Ser  Pro  Asn
    145                      150                      155                           160

Gln  Val  Ser  Gly  Asn  Gly  Asp  Trp  Ala  Gln  Leu  Glu  Gly  Gly  Ile  Gln
                        165                      170                      175

Asn  Asn  Gln  Gln  Thr  Ile  Gln  Gly  Pro  Arg  Ser  Ser  Gln  Ile  Phe  Leu
                   180                      185                      190

Pro  Thr  Ile  Pro  Pro  Leu  Tyr  Ile  Leu  Ser  Asp  Gly  Thr  Ile  Ala  Pro
              195                      200                      205

Val  Val  His  Leu  Phe  Ile  Lys  Pro  Ile  Tyr  Ala  Met  Arg  Ser  Leu  Thr
         210                      215                      220

Lys  Gly  Asp  Thr  Gly  Gln  Ser  Leu  Tyr  Lys  Ile  Lys  Leu  Ala  Ser  Val
    225                      230                      235                           240

Pro  Asn  Gly  Leu  Asn  Leu  Phe  Cys  Asn  Pro  Gly  Tyr  Ala  Phe  Asp  Ser
                        245                      250                      255

Ala  Tyr  Lys  Phe  Leu  Phe  Arg  Pro  Gly  Lys  Asp  Asp  Arg  Thr  Lys  Ser
                   260                      265                      270

Leu  Leu  Gln  Lys  Arg  Val  Arg  Val  Asp  Leu  Arg  Val  Leu  Asp  Lys  Ile
                   275                      280                      285

Gly  Pro  Arg  Val  Met  Thr  Ile  Asp  Met  Asp  Lys
              290                      295

( 2 ) INFORMATION FOR SEQ ID NO:4:

( i ) SEQUENCE CHARACTERISTICS:
        ( A ) LENGTH: 6 base pairs
        ( B ) TYPE: nucleic acid
        ( C ) STRANDEDNESS: unknown (D) TOPOLOGY: unknown (ii) MOLECULE TYPE: DNA (genomic)

(xi) SEQUENCE DESCRIPTION: SEQ ID NO:4:

WGGCCW                                                                                                     6

(2) INFORMATION FOR SEQ ID NO:5:

(i) SEQUENCE CHARACTERISTICS:
        (A) LENGTH: 6 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:5:

RGCGCY                                                                                                      6

(2) INFORMATION FOR SEQ ID NO:6:

(i) SEQUENCE CHARACTERISTICS:
        (A) LENGTH: 4 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:6:

GGCC                                                                                                         4

(2) INFORMATION FOR SEQ ID NO:7:

(i) SEQUENCE CHARACTERISTICS:
        (A) LENGTH: 6 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:7:

GAATTC                                                                                                       6

(2) INFORMATION FOR SEQ ID NO:8:

(i) SEQUENCE CHARACTERISTICS:
        (A) LENGTH: 11 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (D) OTHER INFORMATION: /note="N =Xaa"

(xi) SEQUENCE DESCRIPTION: SEQ ID NO:8:

GCCNNNNNGG C                                                                                                 11

(2) INFORMATION FOR SEQ ID NO:9:

(i) SEQUENCE CHARACTERISTICS:
        (A) LENGTH: 8 base pairs
        (B) TYPE: nucleic acid
        (C) STRANDEDNESS: unknown
        (D) TOPOLOGY: unknown (ii) MOLECULE TYPE: DNA (genomic)

( x i ) SEQUENCE DESCRIPTION: SEQ ID NO:9:

CCCTAGGG                                                                                                    8

( 2 ) INFORMATION FOR SEQ ID NO:10:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:10:

Met Tyr Asn Leu His Arg Glu Lys Ile Trp Met Xaa Tyr Asn Xaa Asn
1               5                   10                  15

Lys Gln Tyr Leu Xaa Asp Asn
            20

( 2 ) INFORMATION FOR SEQ ID NO:11:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: unknown ( i i ) MOLECULE TYPE: protein ( i x ) FEATURE:
        ( D ) OTHER INFORMATION: /note="At position 3, 6, 9 - R = A
            or G, Y = C or T, H = A or C or T"

( x i ) SEQUENCE DESCRIPTION: SEQ ID NO:11:

GARAARATH TGGATG                                                                                15

( 2 ) INFORMATION FOR SEQ ID NO:12:

( i ) SEQUENCE CHARACTERISTICS:
        ( A ) LENGTH: 14 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( D ) OTHER INFORMATION: /note="At position 3, 6, 7, 9, 12
            and 13, R = A or G, Y = C or T, H = A or C or T."

( x i ) SEQUENCE DESCRIPTION: SEQ ID NO:12:

AAYAARCARTAYYT                                                                                  14

( 2 ) INFORMATION FOR SEQ ID NO:13:

( i ) SEQUENCE CHARACTERISTICS:
        ( A ) LENGTH: 29 base pairs
        ( B ) TYPE: nucleic acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:13:

TGTATAATTT ACATAGAGAA AAAATTTGG                                                                 29